United States Patent
Peleg

(10) Patent No.: US 9,342,881 B1
(45) Date of Patent: May 17, 2016

(54) SYSTEM AND METHOD FOR AUTOMATIC DETECTION OF IN VIVO POLYPS IN VIDEO SEQUENCES

(71) Applicant: GIVEN IMAGING LTD., Yoqneam (IL)

(72) Inventor: Dori Peleg, Haifa (IL)

(73) Assignee: GIVEN IMAGING LTD., Yoqneam (IL)

( * ) Notice: Subject to any disclaimer, the term of this patent is extended or adjusted under 35 U.S.C. 154(b) by 0 days.

(21) Appl. No.: 14/554,934

(22) Filed: Nov. 26, 2014

Related U.S. Application Data

(60) Provisional application No. 61/922,230, filed on Dec. 31, 2013, provisional application No. 61/935,420, filed on Feb. 4, 2014.

(51) Int. Cl.
| | |
|---|---|
| G06K 9/00 | (2006.01) |
| G06T 7/00 | (2006.01) |
| A61B 1/04 | (2006.01) |
| A61B 1/00 | (2006.01) |

(52) U.S. Cl.
CPC ........... *G06T 7/0012* (2013.01); *A61B 1/00016* (2013.01); *A61B 1/041* (2013.01); *G06T 7/0085* (2013.01); *G06T 2207/10016* (2013.01); *G06T 2207/10068* (2013.01); *G06T 2207/30032* (2013.01)

(58) Field of Classification Search
None
See application file for complete search history.

(56) References Cited

U.S. PATENT DOCUMENTS

| | | | |
|---|---|---|---|
| 3,683,389 | A | 8/1972 | Hollis |
| 3,888,237 | A | 6/1975 | Mori |
| 3,971,362 | A | 7/1976 | Pope et al. |
| 4,278,077 | A | 7/1981 | Mizumoto |
| 4,689,621 | A | 8/1987 | Kleinberg |
| 4,741,327 | A | 5/1988 | Yabe |

(Continued)

FOREIGN PATENT DOCUMENTS

| | | |
|---|---|---|
| DE | 34 40 177 | 5/1986 |
| EP | 1 260 176 | 11/2002 |

(Continued)

OTHER PUBLICATIONS

Anil K. Jain, "Fundamentals of Digital Image Processing", Prentice Hall 1989, pp. 347-357.

(Continued)

*Primary Examiner* — Nancy Bitar
(74) *Attorney, Agent, or Firm* — Pearl Cohen Zedek Latzer Baratz LLP

(57) ABSTRACT

A system and method for identifying an in-vivo image frame with one or more polyps. Center points of candidate imaged structures may be determined, each center point defining a respective circle. Polyp edge scores may be computed for a plurality of points around each center point, each polyp edge score measuring the coincidence of a respective candidate imaged structure and its respective circle. For each center point, a plurality of edge points of the respective candidate imaged structure may be detected based on the polyp edge score and a candidate imaged structure may be identified based on the detected edge points. For each candidate imaged structure, a candidate polyp may be identified for which extrapolating the detected edge points forms an edge in a shape approximating an ellipse. Image frames with candidate polyps contributing to an above threshold overall image score are determined and marked to include a polyp.

20 Claims, 27 Drawing Sheets

(56) References Cited

U.S. PATENT DOCUMENTS

| | | |
|---|---|---|
| 4,844,076 A | 7/1989 | Lesho et al. |
| 4,915,113 A | 4/1990 | Holman |
| 4,936,823 A | 6/1990 | Colvin et al. |
| 5,279,607 A | 1/1994 | Schentag et al. |
| 5,421,337 A | 6/1995 | Richards-Kortum et al. |
| 5,604,531 A | 2/1997 | Iddan et al. |
| 5,697,384 A | 12/1997 | Miyawaki et al. |
| 5,819,736 A | 10/1998 | Avny et al. |
| 5,833,603 A | 11/1998 | Kovacs et al. |
| 5,853,005 A | 12/1998 | Scanlon |
| 5,993,378 A | 11/1999 | Lemelson |
| 6,010,453 A | 1/2000 | Fiddian-Green |
| 6,074,349 A | 6/2000 | Crowley |
| 6,165,128 A | 12/2000 | C'espedes et al. |
| 6,240,312 B1 | 5/2001 | Alfano et al. |
| 6,266,550 B1 | 7/2001 | Selmon et al. |
| 6,285,897 B1 * | 9/2001 | Kilcoyne ............ A61B 5/0031 128/903 |
| 6,526,299 B2 * | 2/2003 | Pickard ............... A61B 5/0059 600/310 |
| 7,009,634 B2 | 3/2006 | Iddan et al. |
| 8,423,123 B2 | 4/2007 | Horn |
| 7,454,045 B2 | 11/2008 | Yao et al. |
| 7,480,401 B2 | 1/2009 | Shen et al. |
| 8,861,783 B1 * | 10/2014 | Peleg .................... G06T 7/0014 382/100 |
| 8,873,816 B1 * | 10/2014 | Peleg ................. G06K 9/00147 382/128 |
| 8,923,585 B1 * | 12/2014 | Peleg .................... G06T 7/0012 382/128 |
| 9,060,673 B2 * | 6/2015 | Krupnik ................ G06T 3/4038 |
| 2002/0103417 A1 | 8/2002 | Gazdzinski |
| 2003/0167000 A1 | 9/2003 | Mullick et al. |
| 2003/0208107 A1 | 11/2003 | Refael |
| 2005/0078858 A1 | 4/2005 | Yao et al. |
| 2005/0096712 A1 | 5/2005 | Abraham-Fuchs et al. |
| 2006/0164511 A1 | 7/2006 | Krupnik |
| 2006/0247514 A1 | 11/2006 | Panasyuk et al. |
| 2007/0024946 A1 | 2/2007 | Panasyuk et al. |
| 2009/0244260 A1 * | 10/2009 | Takahashi .......... A61B 1/00172 348/45 |
| 2012/0113239 A1 * | 5/2012 | Krupnik ............. A61B 1/00009 348/65 |
| 2013/0028470 A1 * | 1/2013 | Kanda ................ G06K 9/00751 382/103 |
| 2013/0109915 A1 * | 5/2013 | Krupnik ................ G06T 3/4038 600/109 |

FOREIGN PATENT DOCUMENTS

| | | |
|---|---|---|
| WO | WO 01/78017 | 10/2001 |
| WO | WO 2004/058041 | 7/2004 |
| WO | WO 2005/062715 | 7/2005 |

OTHER PUBLICATIONS

Zigang Wang et al., "Feature-Based Texture Display for Detection of Polyps on Flattened Colon Volume", Proceedings of the 2005 IEEE (Engineering in Medicine and Biology 27th Annual Conference), Shanghai, China, Sep. 2005; pp. 1-4.

U.S. Appl. No. 14/503,486, filed Oct. 1, 2014, Peleg.

* cited by examiner

SYSTEM AND METHOD FOR AUTOMATIC DETECTION OF IN VIVO POLYPS IN VIDEO SEQUENCES

CROSS-REFERENCE TO RELATED APPLICATIONS

This application claims the benefit of prior U.S. Provisional Application Ser. No. 61/922,230, filed Dec. 31, 2013 and U.S. Provisional Application Ser. No. 61/935,420, filed Feb. 4, 2014, both of which are incorporated by reference herein in their entireties.

FIELD OF EMBODIMENTS OF THE INVENTION

The present invention relates to systems and methods for analyzing an image stream captured in-vivo. More specifically, the present invention relates to systems and methods for automatically detecting polyps in the in-vivo image stream.

BACKGROUND

A polyp is a growth of tissue raised from a membrane. Polyps may form along the inner lining of a gastro-intestinal (GI) tract and may be of interest to doctors for clinical diagnosis.

In-vivo imaging systems may be employed via an ingestible capsule to provide automated imaging of in-vivo lumens within a patient, such as, the GI tract. The imaging system captures and transmits images of the passage or cavity to an external recording device while passing through the body. The images, when combined in sequence, may form a moving image stream of the passage. The image stream recording the passage of the capsule through the patient may include many (e.g. 50,000) image frames. For a doctor or technician to review such a lengthy image sequence is generally impractical or impossible.

Accordingly, it may be desirable to have a system to automatically detect polyps in the in-vivo image stream. However, polyps may be difficult to detect, for example, due to the variety of polyp forms (e.g. polyps differ in size, shape, definition of edges, closed or open edges, color, etc.), false positive detection due to similar looking shapes (e.g. the circular opening of the in-vivo lumen passageway, closed-loop blood vessels, folds, bubbles, etc.), and/or imaging artifacts (shadows, occluded areas, etc.).

SUMMARY OF EMBODIMENTS OF THE INVENTION

There is an unmet need for, and it would be highly useful to have, a system and method for automatically detecting polyps in an in-vivo image sequence.

In an embodiment of the invention, a system and method is provided for identifying one or more candidate polyps in an in-vivo image frame. An image frame may be received of a body lumen captured in vivo. One or more center points of candidate imaged structures may be determined, each center point defining a respective circle. Polyp edge scores may be computed for a plurality of points around each center point, each polyp edge score measuring the coincidence of a respective candidate imaged structure and its respective circle. For each center point, a plurality of edge points of the respective candidate imaged structure may be detected based on the polyp edge score and a candidate imaged structure may be identified based on the detected edge points. For each candidate imaged structure, a candidate polyp may be identified for which extrapolating the detected edge points forms an edge in a shape approximating an ellipse. One or more feature scores may be generated for one or more respective features for each of one or more candidate polyps in the image frame. The feature scores for each of the candidate polyps in the image may be combined to generate an overall image score. The image frame may be identified to include at least one verified candidate polyp if the overall image score satisfies a predetermined threshold.

BRIEF DESCRIPTION OF THE DRAWINGS

The principles and operation of the system and method according to the present invention may be better understood with reference to the drawings, and the following description, it being understood that these drawings are given for illustrative purposes only and are not meant to be limiting, wherein.

Figure 1:
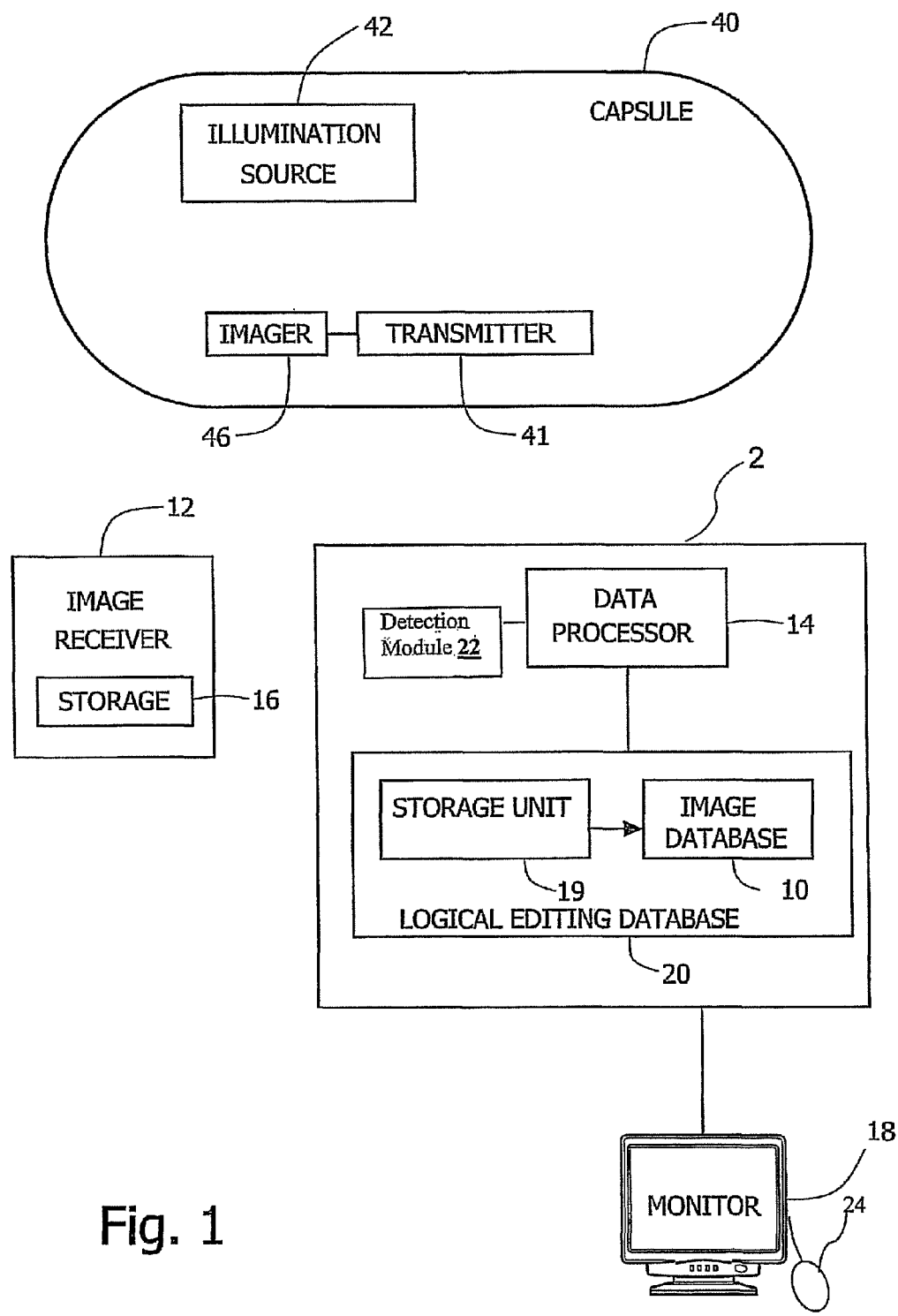
FIG. 1 is a schematic illustration of an in-vivo imaging system, according to an embodiment of the present invention.

It will be appreciated that for simplicity and clarity of illustration, elements shown in the figures have not necessarily been drawn to scale. For example, the dimensions and/or aspect ratio of some of the elements may be exaggerated relative to other elements for clarity. Further, where considered appropriate, reference numerals may be repeated among the figures to indicate corresponding or analogous elements throughout the serial views.

DETAILED DESCRIPTION OF EMBODIMENTS OF THE INVENTION

In the following description, various aspects of the present invention will be described. For purposes of explanation, specific configurations and details are set forth in order to provide a thorough understanding of the present invention. However, it will also be apparent to one skilled in the art that the present invention may be practiced without the specific details presented herein. Furthermore, well known features may be omitted or simplified in order not to obscure the present invention.

Unless specifically stated otherwise, as apparent from the following discussions, it is appreciated that throughout the specification discussions utilizing terms such as "processing", "computing", "storing", "determining", or the like, refer to the action and/or processes of a computer or computing system, or similar electronic computing device, that manipulate and/or transform data represented as physical, such as electronic, quantities within the computing system's registers and/or memories into other data similarly represented as physical quantities within the computing system's memories, registers or other such information storage, transmission or display devices.

Embodiments of the present invention may include apparatuses for performing the operations herein. Such apparatuses may be specially constructed for the desired purposes, or may comprise computers or processors selectively activated or reconfigured by a computer program stored in the computers. Such computer programs may be stored in a computer readable storage medium, such as, but not limited to, any type of disk including floppy disks, optical disks, CD-ROMs, magnetic-optical disks, read-only memories (ROMs), random access memories (RAMs) electrically programmable read-only memories (EPROMs), electrically erasable and programmable read only memories (EEPROMs), magnetic or optical cards, or any other type of media suitable for storing electronic instructions, and capable of being coupled to a computer system bus. It will be appreciated that a variety of programming languages may be used to implement the teachings of the invention as described herein.

Embodiments of the invention may include an article such as a computer or processor readable non-transitory storage medium, such as for example a memory, a disk drive, or a USB flash memory encoding, including or storing instructions, e.g., computer-executable instructions, which when executed by a processor or controller, cause the processor or controller to carry out methods disclosed herein.

Some embodiments of the present invention are directed to a typically swallowable in-vivo device, such as an autonomous swallowable imaging device. Other embodiments need not be swallowable or autonomous, and may have other shapes or configurations. Devices according to embodiments of the present invention, including imaging, receiving, processing, storage and/or display units suitable for use with embodiments of the present invention, may be similar to embodiments described in U.S. Pat. No. 7,009,634 and/or in U.S. Pat. No. 5,604,531, each of which are assigned to the common assignee of the present invention and each of which are hereby incorporated by reference in their entirety. Of course, devices and systems as described herein may have other configurations and other sets of components.

An autonomous in-vivo imaging device may move through the body lumen by peristalsis. Depending on the structure and movement of the endoluminal passageway, the imaging device may move at a variable speed, for example, relatively faster through larger unobstructed passages and relatively slower through narrow or blocked passageways. When the imaging device captures images at a fixed rate (for example, two or four frames per second (fps)), the physical distance between objects being imaged in consecutive frames is also variable, for example, relatively closer when the imaging device moves at a relatively slow speed and relatively farther when the imaging device moves at a relatively fast speed. When the images are combined, in sequence, to form a moving image, the disparity in the proximity of in-vivo objects may generate a skewed or distorted view of the body lumen.

Embodiments of the invention may provide a system and method for automatically identifying one or more candidate polyps in an in-vivo image frame from the in-vivo image sequence. In one embodiment, a plurality of frames forming a subset of the image sequence that satisfy one or more predetermined criteria (e.g. a frame neighboring a detected polyp frame, a frame with an above threshold amount of red color, etc.) and/or excluding a subset of frames (e.g. image frames or image regions within the frames covered by an above threshold surface area of content, bubbles or black/darkness, redundant frames that substantially match a previous frame, etc.) may be selected for polyp investigation. Alternatively, the entire set of frames of the image sequence may be selected.

Figure 3:
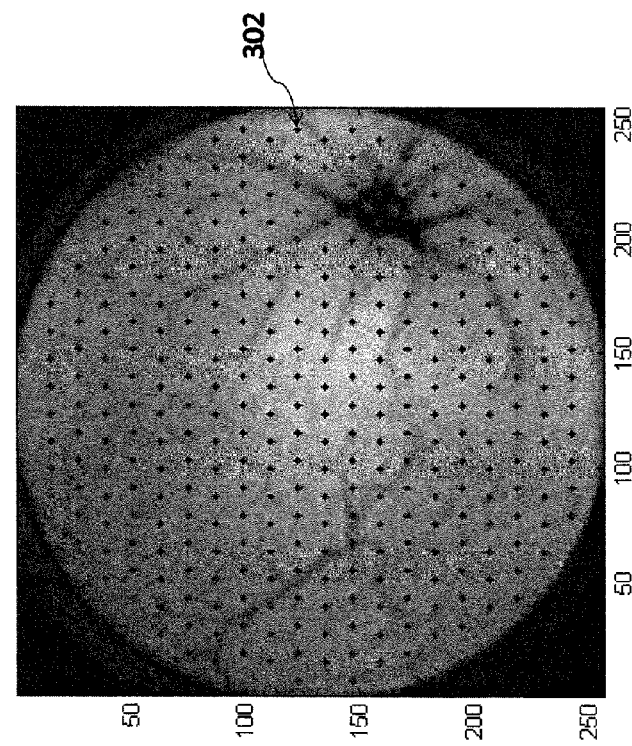
FIG. 3 shows an image frame overlaid with a plurality of center points of candidate circles for polyps, according to an embodiment of the present invention.

Each of the selected frames may be segmented or divided into a plurality of regions that may be analyzed to detect if an imaged structure therein is a candidate polyp. The image may be segmented by generating a plurality of points within the image, each point defining the center of a distinct region (e.g. adjacent regions may or may not overlap). The center points may be arranged, for example, in a lattice (e.g. as shown in FIG. 3). Regions may be circular, elliptical, square, rectangular or may have any other polygonal or two-dimensional shape. Each region may have a size that is predetermined (e.g. a fixed radius extending from the center point to the region's edge) or variable (e.g. a dynamic radius adjusted based on the scale or estimated distance of the camera to the images structures, or as an upper bound of the maximum detected polyp size in the patient or image sequence, or other criteria). The size of each region may be determined based on an edge detected for each region (e.g. the size may define an areas having a radius that is a predetermined number greater than 1, such as 1.5, times the average edge radius). An edge may be detected based, for example, on calculation of the gradient of rays projected from each center point, and each region may be analyzed to identify a candidate polyp. For each center point, edge points may be detected for example using a polyp edge score. Since imaged polyp edges are generally elliptical shaped or curved, the polyp edge score may measure the degree to which edge points of the imaged structure coincide or match an ellipse or circle centered at the center point of the region. The polyp edge score may be, for example, a function of the product of the gradient of the image intensity values $\nabla I$ and the gradient of an ellipse $\nabla E$ or circle $\nabla C$. When the edge of the imaged structure coincides with the ellipse or circle, their respective gradients coincide, and the polyp edge score is relatively high. Conversely, when the edge of the imaged structure does not coincide with the ellipse or circle, their respective gradients do not coincide, and the polyp edge score is relatively low. The polyp edge score may be compared to one or more thresholds or threshold ranges to distinguish edge points (e.g. having an above threshold polyp edge score) from other structures (e.g. having a below threshold polyp edge score).

Once the edge points are detected, a circular or elliptical edge may be extrapolated to trace, approximate or fit the detected edge points, for example, using a least squares approximation. Outlier edge points deviating from the average or median radius by more than a predetermined or calculated threshold may be eliminated. This may significantly reduce errors, which square in value when using a least square approximation. The circular or elliptical edge may encircle or define a candidate polyp. The extrapolated circle or ellipse defining the polyp edge is typically different than (but may be the same) as the ellipse (E) used to calculate the polyp edge score and the two ellipses may have different (or the same) center points. One or more (e.g. tens or hundreds) candidate polyps may be identified in each image frame.

Once the candidate polyps are identified, features or traits of each candidate polyp may be scored and analyzed to confirm or reject the presence of polyps in each frame. Features may include the polyp edge feature having a score that measures the coincidence of the polyp edge with an ellipse, an angle feature having a score that measures the amount that the detected candidate polyp edge coincides with the approximated ellipse, a fold feature having a score that measures folds inside the polyp candidate e.g. to eliminate false interior edges, a hue feature having a score that measures the relative hue of the candidate polyp interior and edge e.g. to validate or increase the image score for images with candidate polyps having a greater hue along their edge than throughout their interior, a saturation feature having a score that measures the relative saturation of the polyp interior and edge e.g. to validate or increase the image score for images with candidate polyps having a higher saturation along its edge than throughout its interior, an intensity feature having a score that measures the average intensity of the polyp e.g. to validate or increase the image score for images with candidate polyps having relatively high intensity due to the typical protrusion of polyps close to the imager/camera, a redness feature having a score that measures the relative amount of red color of the polyp interior and edge e.g. to validate or increase the image score for images with candidate polyps having more red color inside the polyp than along its edge which may eliminate false detection of blood vessels, e.g. veins, that form an elliptical shape and as such, have a significantly higher red score along the edge of the candidate than in the interior of the candidate, an edge perimeter feature having a score that measures fold scores along the polyp edge e.g. to validate or increase the image score for images with candidate polyps having edges that form approximately full ellipses, a content feature having a minimum content score that measures the minimum content value of the candidate polyp e.g. to validate or increase the image score for images with candidate polyps having little or no content and/or a 10% content score that measures the $10^{th}$ percentile of content values of the candidate polyp e.g. to validate or increase the image score for images with candidate polyps having less than 10% content, a white feature having a score that measures the maximum white value inside of the polyp e.g. to eliminate or decrease the image score for images with candidate polyps that are bubbles which have white glare in their interiors, and/or a relative red feature having a score that measures the relative amount of red color inside the candidate polyp compared to the rest of the image e.g. to validate or increase the image score for images with candidate polyps that are significantly red such as tumor or bleeding polyps.

Feature scores for one or more candidate polyps in an image frame may be input into a classifier. The classifier may combine all the feature scores for all candidate polyps into an overall image score or a combined image score, or may analyze all feature scores for each candidate polyp individually. The final feature score may be the maximum feature score for all candidates in the image or for each individual candidate. The classifier may divide images into groups of images that have one or more verified candidate polyps (1) (e.g. images that have an above threshold overall image score) or images that have no verified candidate polyps (−1) (e.g. having a below threshold overall image score). That is, in one embodiment, all candidate polyps in an image are evaluated together by combining their individual polyp edge scores into an overall image score and the group of polyp candidates in the image are "verified" when the overall image score is above a threshold. In another embodiment, each candidate polyp may be evaluated and verified individually, for example, when its individual associated polyp edge score is above a threshold. In such cases, any image with one or more individually verified candidate polyp may be marked as a polyp image. The threshold may be determined by using a training set of manually marked images, predetermined to include polyps or not and training the classifier to match the results of the training set. In some embodiments, the classifier may indicate a probability or size/shape of a polyp in the image frame based on the overall image score.

Once the one or more candidates are verified or confirmed to be potential or likely polyps, the polyps and/or polyp image frames or scenes may be flagged, marked, highlighted or otherwise differentiated from non-polyp imaged structures or non-polyp image frames or scenes, for example, to be separately stored and/or displayed. In one embodiment, the subset of image sequence frames confirmed to have polyps may be extracted from the image sequence and stored separately therefrom in a different memory area to generate a distinct image stream or arrangement of still images. In another embodiment, the subset of polyp frames may remain in the original image stream but may be individually addressed to be separately extracted from the shared memory. In one embodiment, the image sequence may have different playback modes: (1) a regular playback mode e.g. playing the entire image sequence including polyp and non-polyp frames and (2) an abridged polyp frame playback mode e.g. playing only the subset of polyp frames and skipping the non-polyp frames. In one example, a user may incrementally scan the polyp frames as still images, e.g., progressing through the sequence using a mouse or other input device. In another example, a user may playback the polyp frames as a single continuous movie, or as multiple polyp scenes, each scene including a cluster of (e.g. adjacent or neighboring) frames depicting the same one or more polyps. In yet another example, the overall image score may be used, along with other pathology detectors and image analysis logic, to determine which frames should be marked, displayed to a user, or used to generate a summary image stream from the original set of image frames. In some embodiments, the overall image score may be used, e.g. individually or along with other pathology detectors and image analysis logic, to determine which frames should be included in an array of images which may be displayed to a user as an image stream preview of candidate pathologies, e.g. as disclosed in US Patent Application Publication Number 2013/0109915 to Krupnik et al., assigned to the common assignee of the present invention.

The location, size, shape, color and/or other features of the confirmed polyps may be recorded and marked or displayed e.g. together with the associated polyp frames. The location may specify the region of the lumen, a distance from the beginning of the GI tract or from the entrance to the current organ, or other distance or length (e.g. the location being independent of the frame number or time of traversal). The size of the polyp may be normalized or scaled based on the estimated distance of the camera to the imaged structures, for example, to reduce camera distortions. The color of a polyp may be filtered or normalized based on an average color or color spectrum of the frame or image stream, for example, to reduce imaging artifacts and isolate redness due to blood. The shape of the polyp may indicate e.g. the general curvature, protrusion or elongation of the polyp, such as, round, elliptical, raised, etc. Polyp frames may be filtered for selection or playback based on their associated location, size, shape and/or color, e.g., to display only colon polyps, large polyps or substantially red polyps.

Reference is made to FIG. 1, which schematically illustrates an in-vivo imaging system according to an embodiment of the invention.

According to some embodiments, a system may include a device, for example, an imaging device 40. Imaging device 40 may be a swallowable in-vivo imaging device, but other sorts of devices or suitable implementations may be used. According to one embodiment, imaging device 40 may communicate with an external receiving and display system to provide display of data, control, or other functions. For example, power may be provided by an internal battery or a wireless receiving system. Other embodiments may have other configurations and capabilities.

Imaging device 40 may include an imager 46, for capturing images, an illumination source 42, for illuminating the body lumen, and a transmitter 41, for transmitting image and possibly other information to a receiving device. Transmitter 41 may include receiver capability, for example, to receive control information. An optical system, including, for example, lenses or mirrors, may aid in focusing reflected light onto the imager 46.

An image receiver 12, which may include an antenna or antenna array, an image receiver storage unit 16, a data processor 14, a data processor storage unit 19, and an image monitor 18, for displaying, for example, the images recorded by the imaging device 40, may be located outside the patient's body in one or more locations. The receiver 12 and image receiver storage unit 16 may be small and portable, and may be worn on the patient's body during recording of the images.

According to one embodiment of the invention, data processor 14, data processor storage unit 19 and monitor 18 may be part of a personal computer or workstation 2 which includes standard components such as a processor, a memory, a disk drive, and input-output devices, although alternate configurations are possible, and the system and method of the present invention may be implemented on various suitable computing systems. An input device 24 may receive input from a user (e.g., via a pointing device, click-wheel or mouse, keys, touch screen, recorder/microphone, other input components) and send corresponding commands to trigger control of the computer components (e.g., data processor 14).

Data processor 14 may include any standard data processor, such as a microprocessor, multiprocessor, accelerator board, or any other serial or parallel high performance data processor. Data processor 14 may be configured to carry out methods of the present invention by, for example, executing code or instructions stored for example in storage unit 19. Data processor 14 may act as or carry out the functionality of detection module 22, logical editing database 20, image monitor 18, input device 24, and image receiver 12.

Image monitor 18 may be a computer screen, a conventional video display, or any other device capable of providing image or other data.

Preferably, the imager 46 is a suitable complementary metal-oxide-semiconductor (CMOS) camera, such as a "camera on a chip" type CMOS imager specified by Given Imaging Ltd. of Israel and designed by Photobit Corporation of California, USA. In alternate embodiments, the imager 46 may be another device, for example, a charge-coupled device (CCD).

The illumination source 42 may be, for example, one or more light emitting diodes, or another suitable light source.

In operation, imager 46 may capture images and send data representing the images to transmitter 41, which transmits images to receiver 12 using, for example, electromagnetic radio waves. Receiver 12 may transfer the image or other received data to storage unit 16. After a certain period of time of data collection, the image data stored in storage unit 16 may be sent to the data processor 14 (e.g., contained within workstation 2) or the data processor storage unit 19. For example, the image receiver storage unit 16 may be taken off the patient's body and connected to the personal computer or workstation 2 which includes the data processor 14 and data processor storage unit 19 via a standard data link, e.g., a serial or parallel interface of known construction. The image data may then be transferred from the image receiver storage unit 16 to the image database 10 within data processor storage unit 19.

Data processor 14 may analyze the data, for example, according to the logical editing database 20, and provide the analyzed data to the image monitor 18, where for example, a health professional views the image data and/or corresponding analyzed data such as polyp edge scores, candidate polyps, features, and/or a computer-generated diagnosis. Data processor 14 may operate software which, in conjunction with basic operating software such as an operating system and device drivers, controls the operation of data processor 14. According to one embodiment, the software controlling data processor 14 may include code written, for example, in the C++ language and possibly alternative or additional languages, and may be implemented in a variety of known methods.

The image data collected and stored may be stored indefinitely, transferred to other locations, or manipulated or analyzed. Data processor 14 may use the images to detect polyps, for example, in the GI tract, and, in addition, the system may provide information about the location, size and/or color of these polyps. While using a system where the data processor storage unit 19 first collects data and then transfers data to the data processor 14, the image data is not viewed in real time, other configurations allow for real time viewing.

According to one embodiment, the imaging device 40 may collect a series of still images as it traverses the GI tract. The images may be later presented as, for example, a stream or sequences of images or a moving image of the traverse of the GI tract. The in-vivo imager system may collect a large volume of data, as the imaging device 40 may take several hours to traverse the GI tract. The imager 46 may record images at a rate of, for example, four to forty images per second (other rates, such as two frames per second, may be used). The imager 46 may have a fixed or variable frame capture and/or transmission rate. When the imager 46 has a variable or adaptive frame rate (AFR), the imager 46 may switch back and forth between frame rates, for example, based on parameters, such as the imaging device 40 speed, estimated location, similarity between consecutive images, or other criteria. A total of thousands of images, for example, 50,000 images, may be recorded. The image recordation rate, the frame capture rate, the total number of images captured, the total number of images selected if the moving image is edited, and the view time of the moving image, may each be fixed or varied.

The image data recorded and transmitted by the imaging device 40 may be digital color image data, although in alternate embodiments other image formats may be used. In one example, each frame of image data may include 256 rows of 256 pixels each, 320 rows of 320 pixels, or 1,000 rows of 1,000 pixels, each pixel including bytes for color and brightness, according to known methods. For example, in each pixel, color may be represented by a mosaic of four sub-pixels, each sub-pixel corresponding to primary color components such as red (R), green (G), or blue (B) (where one primary is represented twice). The intensity or brightness of the overall pixel may be recorded by a one byte (i.e., 0-255) brightness value. According to one embodiment, images may be stored sequentially in data processor storage unit 19. The stored data may include one or more pixel properties, including color and brightness.

While information gathering, storage and processing are described to be performed by certain units, the system and method of the present invention may be practiced with alternate configurations. For example, the components gathering image information need not be contained in an imaging device, but may be contained in any other vehicle suitable for traversing a lumen in a human body, such as an endoscope, stent, catheter, needle, etc.

Storage unit 19 may store a series of images recorded by an imaging device 40. The images the imaging device 40 records as it moves through a patient's GI tract may be combined consecutively to form a moving image stream or video.

A moving image stream captured by the imaging device 40 may include scenes (e.g., a series of images depicting an event, such as, a moving view of the same polyp).

Data processor 14 may execute a segmentation process to divide each of a plurality of image frames into regions having center points. Data processor 14 may include a detection module 22 for automatically detecting edge points and polyps in each region, using storage unit 19, an image database 10 and a logic detection database 20. Storage unit 19 may store images captured by imaging device 40. Image database 10 may store a subset of image sequence frames confirmed to have polyps or may store data pointers, flags, or addresses thereto. Logical detection database 20 may store instructions for execution or rules for use by software for detecting edge points and polyps in captured image(s) from storage unit 19 and/or image database 10. Detection module 22 may use pattern recognition and/or feature extraction logic (for example, from logical detection database 20) to analyze imaged structures as candidate polyps and for example, to detect a size, color, location and/or shape of the polyp in each frame.

Detection module 22 may be a physical device or may be instructions stored in a memory which when executed by a processor, e.g., data processor 14, may perform detection functions. For example, detection module 22 may be executed by a separate processor or may be a dedicated processing module.

Figure 2:
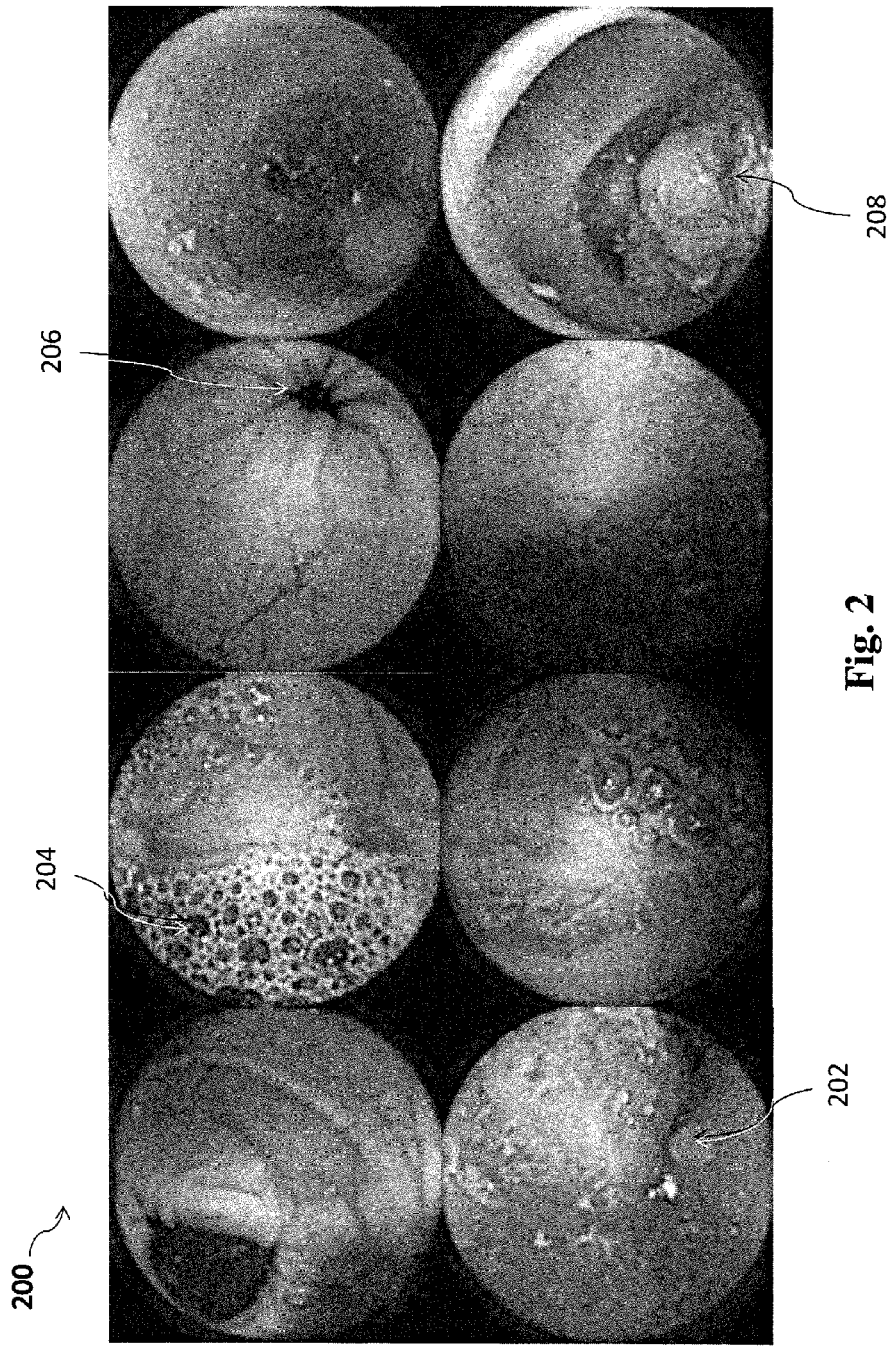
FIG. 2 shows a plurality of in-vivo image frames, according to an embodiment of the present invention.

Reference is made to FIG. 2, which shows a plurality of in-vivo image frames 200, according to an embodiment of the present invention. Image frames 200 may be captured by imager 46 and stored for example in storage unit 19 of FIG. 1.

Image frames 200 may include polyps 202 detected by a processor (e.g. detection module 22). Image frames 200 may also include other non-polyp structures, such as, bubbles 204, lumen opening 206 and growth or content 208, which may resemble polyps 202 and potentially yield false positive results by the processor. The processor may distinguish these structures by executing operations according to embodiments of the invention to confirm or verify candidate structures that are polyps 202 and reject candidate structures that are non-polyps 204-208.

To identify polyps 202, the edge of the polyp may be assumed to be similar to an ellipse and the edges of the polyp may be assumed to be stronger or better-defined than edges detected within the polyp. However, in some examples, detecting polyps 202 may be difficult for example when the edge of the polyp is faint or uneven. To detect such polyps 202, the processor may create a polyp edge score that accentuates the polyp edge based on the assumptions. Once the polyp edge is defined, the edge is fit to an ellipse or to a circle to generate a candidate polyp. The gradient of the edge of a polyp 202 may coincide with the gradient of the ellipse or circle that best approximates or fits the edge.

The formula for an ellipse E that best approximates the edge may be defined for example as follows:

$$X^T*P*X + Q^T*X = r \quad (1)$$

where P is a positive semi-definite matrix of dimension 2×2 having indices P(1,1), P(1,2), P(2,1) and P(2,2), where P(1,1)=1 and P(1,2)=P(2,1), P>=0, X is a matrix of dimension 2×1, Q is matrix of dimension 2×1, the superscript "T" indicates a transpose matrix and r is a scalar value or matrix of dimension 1×1. To determine the gradient $\nabla E = 2*P*X + Q$ of such an ellipse, the processor may solve the four parameters: P(1,2), P(2,2), Q(1,1) and Q(1,2). In some embodiments, to simplify the problem, the processor may approximate the gradient of the ellipse $\nabla E$ as the gradient for a circle $\nabla C$. The equation of the circle C is $(X-Xc)'*(X-Xc)=r^2$, where Xc is a 2×1 vector of the (x,y) coordinates of the center of the circle and r is the radius. Accordingly, the gradient of the circle is $\nabla C = 2(X-Xc)$. The approximation using circle C is typically sufficiently close to the actual calculation using the ellipse E since most polyps 202 are not very elongated and resemble circles. Since the gradient of a circle, $\nabla C = 2(X-Xc)$ is independent of the radius, the processor may solve the circle equation by finding the center of the circle, solving only 2 parameters (the (x, y) coordinates of Xc) instead of 4. Since the center of polyp 202 is unknown, the processor may generate a grid or lattice of candidate center points, e.g., as shown in reference to FIG. 3.

Reference is made to FIG. 3, which shows an image frame 300 overlaid with a plurality of center points 302 of candidate circles for polyps, according to an embodiment of the present invention. The processor may generate a constant grid per video defining the center points 302 of circles. In one example, the grid may include two alternating row grids with a difference of 12 pixels between each pair of adjacent center points 302 and between each pair of adjacent rows. There is for example an offset of six pixels between the rows. A region of interest (ROI) mask defines a region inside of the black circular edge. Center points 302 located outside of the ROI mask contracted radially inward by a disc shape of a predetermined radius (e.g. N=seven pixels) may be discarded. In one example, e.g. for an image of 256×256 pixels, an average of approximately 330 center points 302 are generated in the grid. Any other arrangement of center points 302 or regions or region shapes and sizes may be used.

Figure 4:
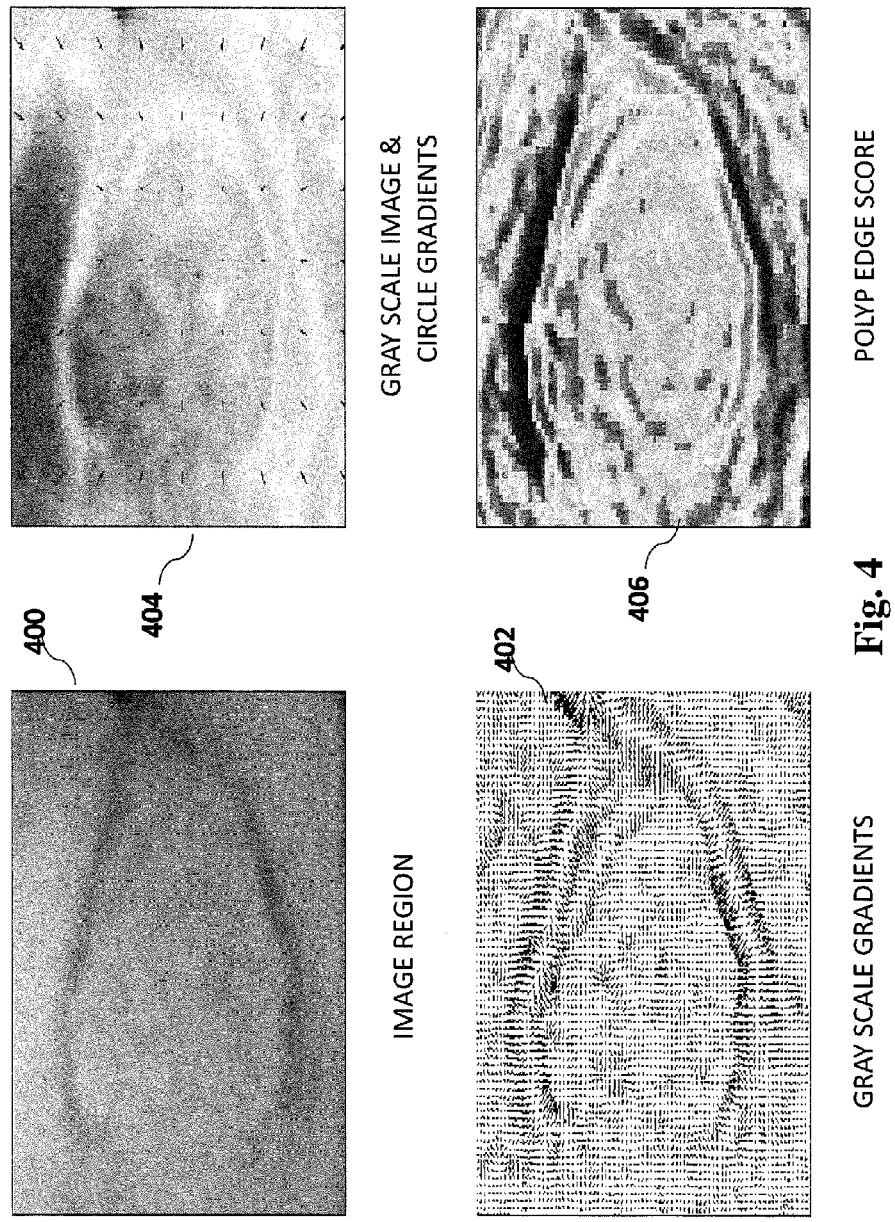
FIG. 4 shows an image region and associated image gradient and circle gradient, which are used to compute polyp edge scores for a region, according to an embodiment of the present invention.

Circles centered at each center point 302 may be used to compute a polyp edge score, e.g., as shown in reference to FIG. 4.

Reference is made to FIG. 4, which shows an image region 400 and associated image gradient 402 and circle gradient 404, which are used to compute polyp edge scores 406 for a region, according to an embodiment of the present invention.

The processor may compute image gradient 402 to be $\nabla I$, where $\nabla$ is the gradient operator of a function $f$ defined by a multi-dimensional derivative $$\nabla f = \frac{\partial f}{\partial x} + \frac{\partial f}{\partial y},$$

which points in the direction of maximal increase of the function $f$, and I is a function of the brightness of the gray scale of image region 400. At the edge of a polyp, there is typically a transition from a relatively darker shadow area to a brighter area in image region 400. Accordingly, the gradients of the image $\nabla I$ within the polyp and near an edge typically point radially inward toward the center point, while the gradients of the image $\nabla I$ outside of the polyp and near an edge typically point radially outward away from the center point.

The processor may compute circle gradient 404 to be $-\nabla C$, where C is the circle centered at the center point of the investigated region.

The processor may compute polyp edge scores 406 for the region to be $PE=\nabla I^T \cdot (-\nabla C)$, which measures the coincidence of the gradient of the image (or gray scale image) function I and the gradient of the circle function C. Since $\nabla C$ points radially outward from the center point and $\nabla I$ points radially inward from the center point, a negative sign is used in the polyp edge score (e.g. $-\nabla C$ or alternatively $-\nabla I$) to align the directions of the gradients of the circle and image functions. The polyp edge score 406 highlights edges of polyps in image region 400 since polyp edges in I align with circle edges in C to generate a relatively high or above threshold polyp edge score. Conversely, polyp edge score 406 suppresses non-edge points of polyps in image region 400 since points in I that do not align with circle edges in C yield a relatively low or below threshold polyp edge score.

Using polyp edge scores 406 generated in FIG. 4, the processor may detect edge points of image region 400, e.g., as shown in reference to FIGS. 5-10.

Figure 5:
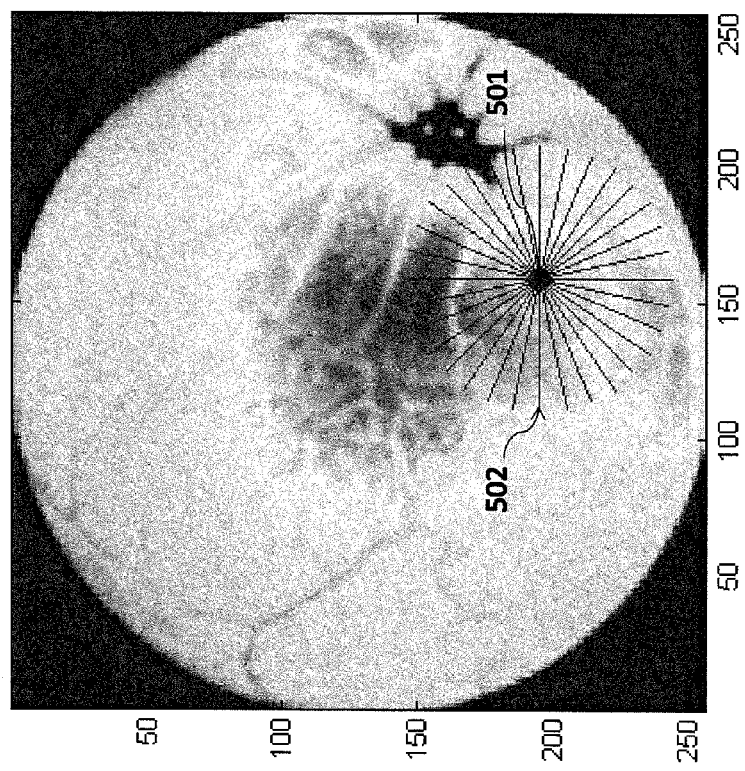
FIG. 5 shows a gray scale image and a plurality of radial lines extending radially outward from the center point along which polyp edge scores may be analyzed, according to an embodiment of the present invention.

Reference is made to FIG. 5, which shows a gray scale image 500 and a plurality of radial lines 502 extending radially outward from the center point 501 along which polyp edge scores may be analyzed, according to an embodiment of the present invention. In the example shown in FIG. 5, a plurality of (e.g. N=32) radial lines 502 project from the center point 501 of circle C at angular intervals of $\pi/16$ radians, although other numbers of (N) radial lines 502 and angular intervals of $2\pi/N$ radians may be used. The radial lines 502 may have a predetermined length, for example, approximating an upper bound of a radius of a typical large polyp. In the example shown in FIG. 5, the line radius is 50 pixels, although other radii may be used.

The processor may search along each line for an edge point. The processor may detect at most one edge point, and in some embodiments no edge points (e.g. when the polyp edge is broken forming an incomplete ellipse or circle).

Figure 6:
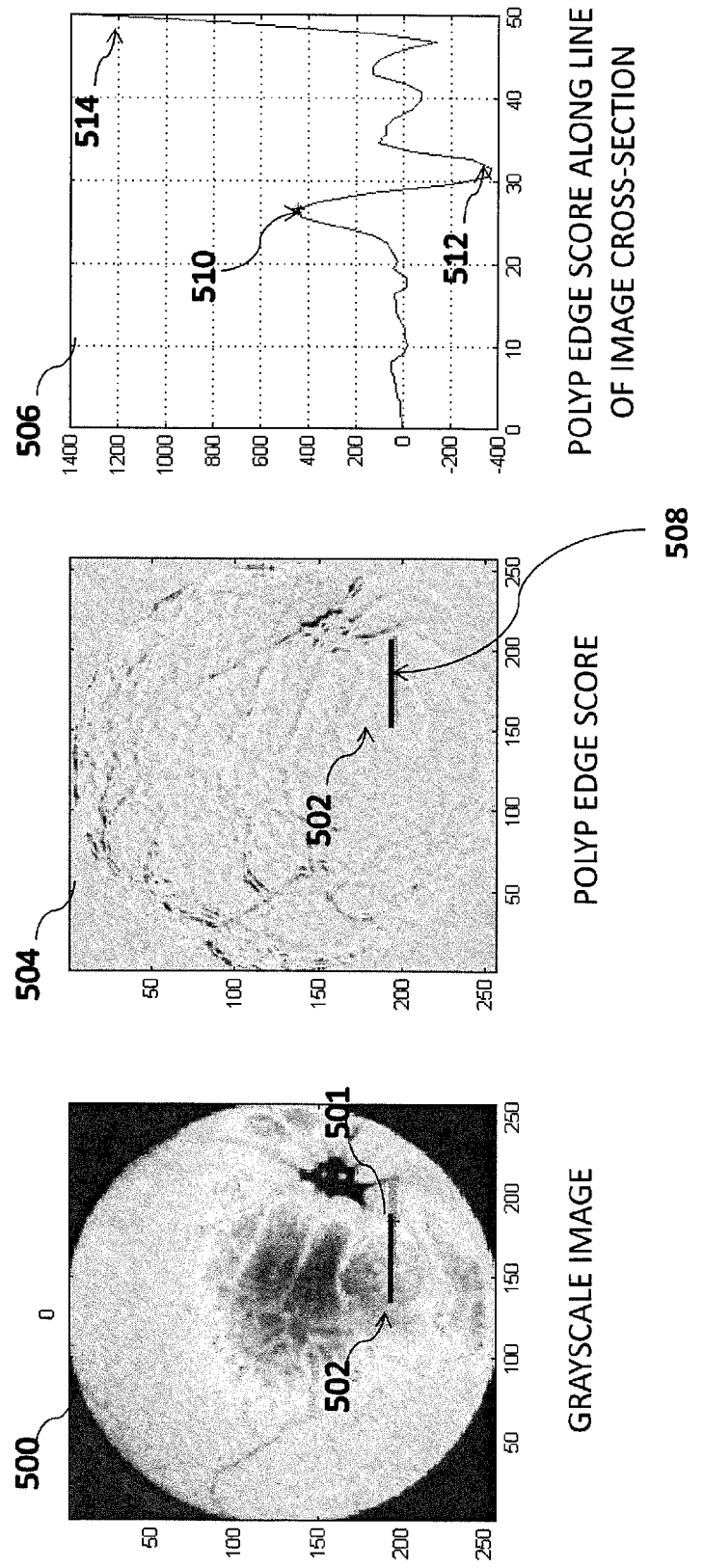
FIG. 6 shows a gray scale image, polyp edge scores thereof, and a graph of polyp edge scores investigated along one of the radial lines of FIG. 5, according to an embodiment of the present invention.

Reference is made to FIG. 6, which shows a gray scale image 500, polyp edge scores 504 thereof, and a graph 506 of polyp edge scores investigated along one of the radial lines 502 of FIG. 5, according to an embodiment of the present invention.

Edge point 508 may have a local maximum polyp edge score 510 (e.g. indicating a prominent edge), a polyp edge score 510 that is greater than that of any radially inward points along radial line 502 (e.g. since edge points on the perimeter of the polyp are typically greater or more prominent than edge points within a polyp), and may be radially inward from a neighboring point that has a local, global or significant minimum polyp edge score 512 (e.g. significant dips in polyp edge score typically occur just outside of the edge). Edge point 508 need not have a global (overall) maximum polyp edge score 514 along radial line 502 since strong edges may occur outside of the polyp.

Figure 7:
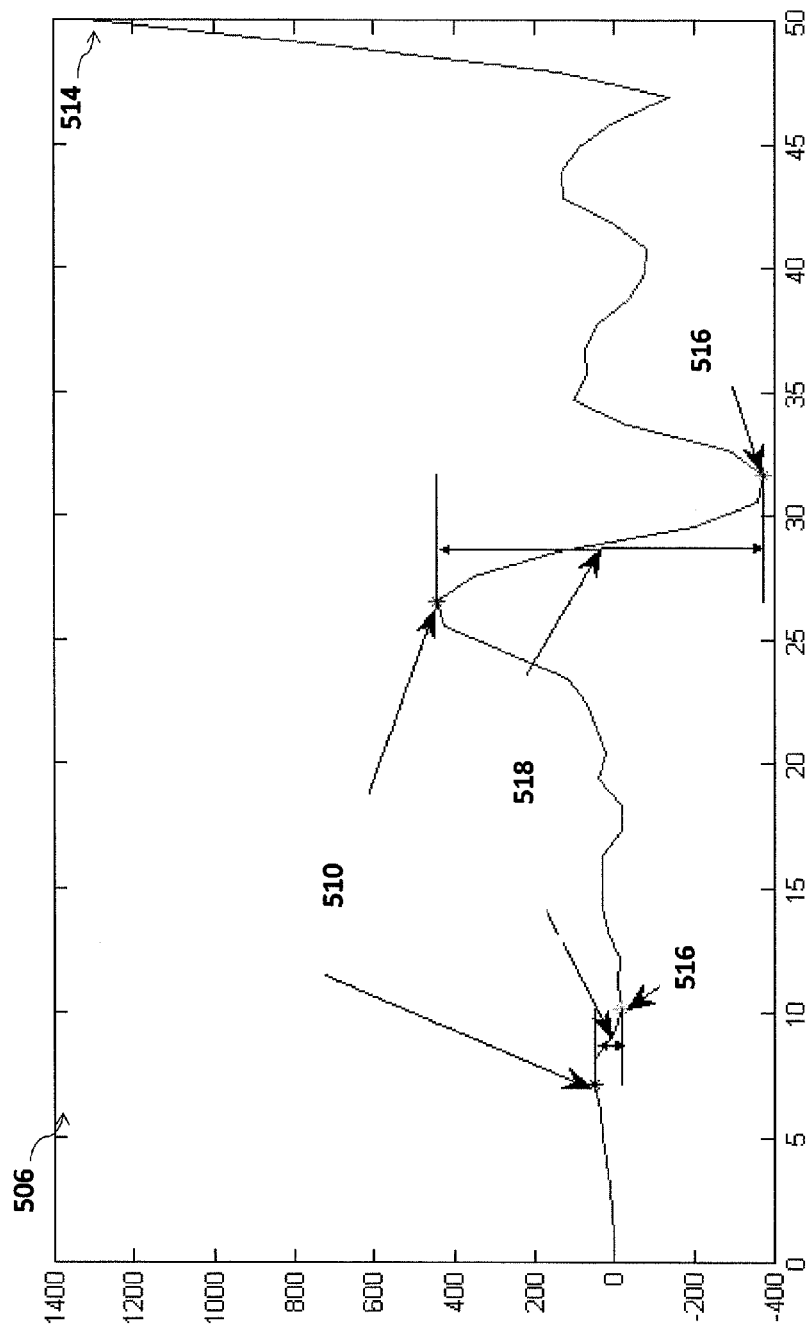
FIG. 7 is graph of polyp edge scores used to detect polyp edge points along radial line of FIGS. 5 and 6, according to an embodiment of the present invention.

The processor may use the polyp edge scores of graph 506 to detect an edge point 508 along radial line 502, e.g., as described in reference to FIG. 7.

Reference is made to FIG. 7, which is graph 506 of polyp edge scores used to detect polyp edge points along radial line 502 of FIGS. 5 and 6, according to an embodiment of the present invention.

The processor may search radial line 502 for candidate edge points 508 that have polyp edge scores 510 that are a local maximum and greater than or equal to the polyp edge scores of all radially inward points along radial line 502 (e.g. the greatest local maxima so far).

For all such candidate edge points 508, the processor may calculate one or more of the following parameters:

Min_between2maxima 516, which is the minimal polyp edge score between the current candidate point and a previous candidate point (or a center point 501 if the current candidate point is the most radially inward candidate point). Min_between2maxima 516 detects the scores of a local minimum polyp edge score between local maxima 510 polyp edge scores of two candidate edge points 508.

Diff_min_between2maxima_prev_max 518, which is the difference between Min_between2maxima 516 and the polyp edge score of the previous (radially inward) candidate point 510 (or of center point 501 if the current candidate point is the most radially inward candidate point). Diff_min_between2maxima_prev_max 518 calculates the difference between a local maximum score 510 and a subsequent local minimum score 516 to determine the difference between scores of a candidate edge point 508 and its radially outward neighboring minimum point. A high Diff_min_between2maxima_prev_max 518 (e.g. at pixel 28) may indicate a significant peak followed by a significant trough in polyp edge scores moving radially outward along radial line 502, which indicates that candidate edge point 508 may be located along a prominent edge.

Rel_score=the polyp edge score of the current candidate point minus the median, mean or mode polyp edge score of points radially inward to the current candidate point along radial line 502. A high Rel_score may indicate that the current candidate point has a greater polyp edge score compared to radially inward points.

Final_score=M*Rel_score+ Diff_min_between2maxima_prev_max, which may indicate the likelihood that the current candidate point is on an edge of a polyp. A polyp edge 508 typically has a relatively high difference in polyp edge score compared to its neighbor (e.g. a high Diff_min_between2maxima_prev_max 518) as well as a relatively high overall polyp score (e.g. a high Rel_score). Accordingly, the final edge score may increase when either of the Diff_min_between2maxima_prev_max or the Rel_score increases. M is an adjustable constant and is, for example, 1.2.

The processor may determine the edge point 508 along each line to be the point from among the candidate points along the line that has the highest Final_score (e.g. at pixel 28 in the example of FIGS. 6-7).

The processor may calculate the point with the lowest Rel_score from among the points with the lowest local minima so far compared to radially inward points. If there are no candidate points or if the detected edge point 508 is radially outward from the point with the lowest Rel_score, the processor may determine that there is no edge point along radial line 502. Since the lowest Rel_score is typically associated with an outer edge point of a polyp, points radially outward therefrom may be eliminated as edge points to reduce false positives of edges outside of a polyp.

Figure 8:
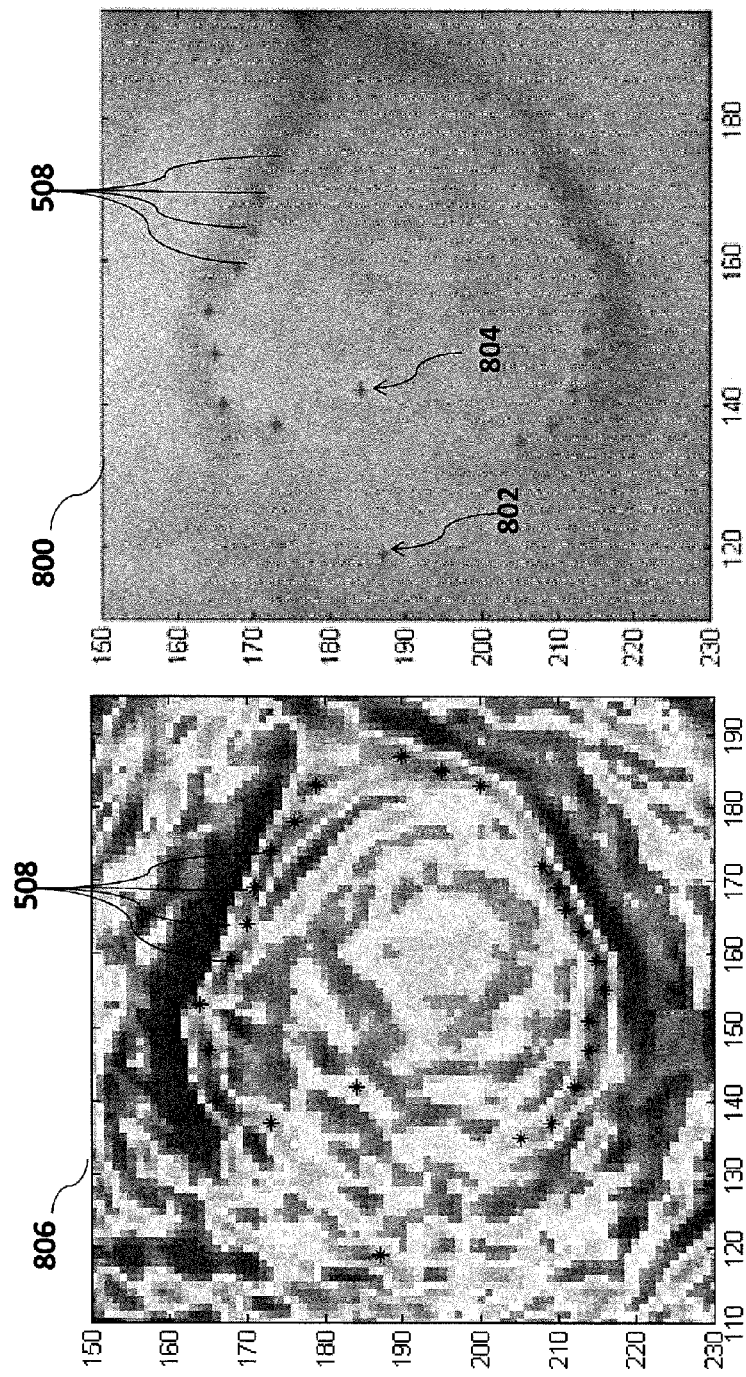
FIG. 8 shows detected edge points and associated polyp edge scores and image region, according to an embodiment of the present invention.

Reference is made to FIG. 8, which shows detected edge points 508 and associated polyp edge scores 806 and image region 800, according to an embodiment of the present invention.

In some examples, edge points 508 may form an incomplete or broken ellipse (e.g. the edge gap along the left side the polyp shown in image region 800) since some lines 502 may have no edge points. In some examples, one or more edge points 508 may be outliers, for example, differing from the mean, median or mode radius by more than a predetermined amount. The processor may remove such outlier edge points 508, e.g., as described in reference to FIG. 9.

Figure 9:
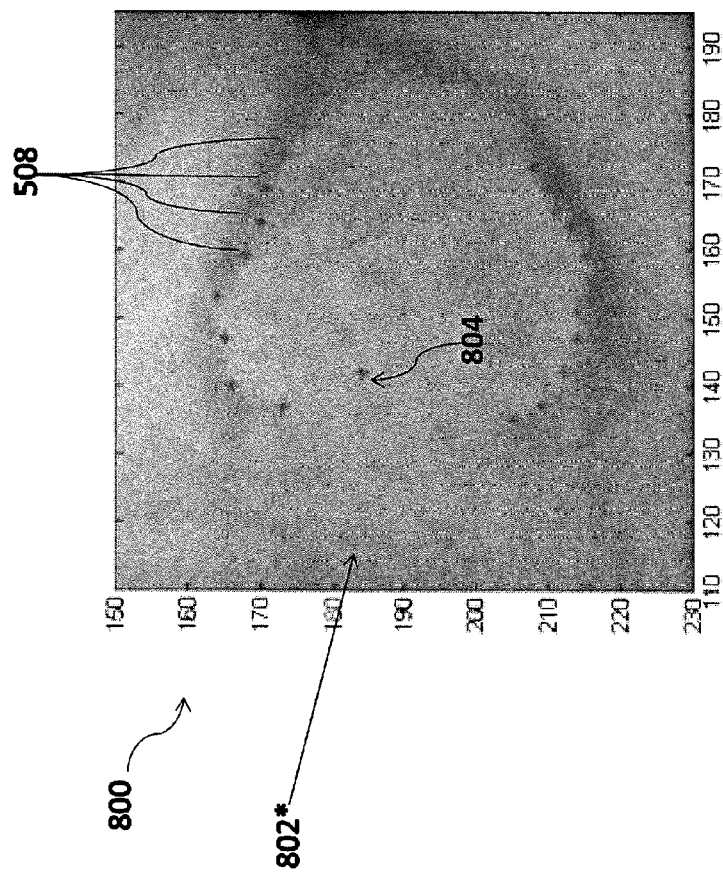
FIG. 9 shows the removal of an outlier edge point from FIG. 8, according to an embodiment of the present invention.

Reference is made to FIG. 9, which shows the removal 802 of an outlier edge point 802 from FIG. 8, according to an embodiment of the present invention.

The processor may calculate the radius of each detected polyp edge points 508 from center point 501 and a nominal radius equal to the mean, median or mode of the radii of all the detected polyp edge 508. The processor may remove or delete all detected polyp edge points 508 x having a radius Rx that is greater than a first predetermined parameter, for example 3/2 of the nominal radius $\overline{Rx}$ or smaller than a second predetermined parameter, for example ⅔ of the nominal radius $\overline{Rx}$ e.g.

$$\begin{cases} \text{if } Rx \geq \frac{3}{2}\overline{Rx} \\ \text{if } Rx < \frac{2}{3}\overline{Rx} \end{cases}.$$

Other parameters may be selected.

Figure 10:
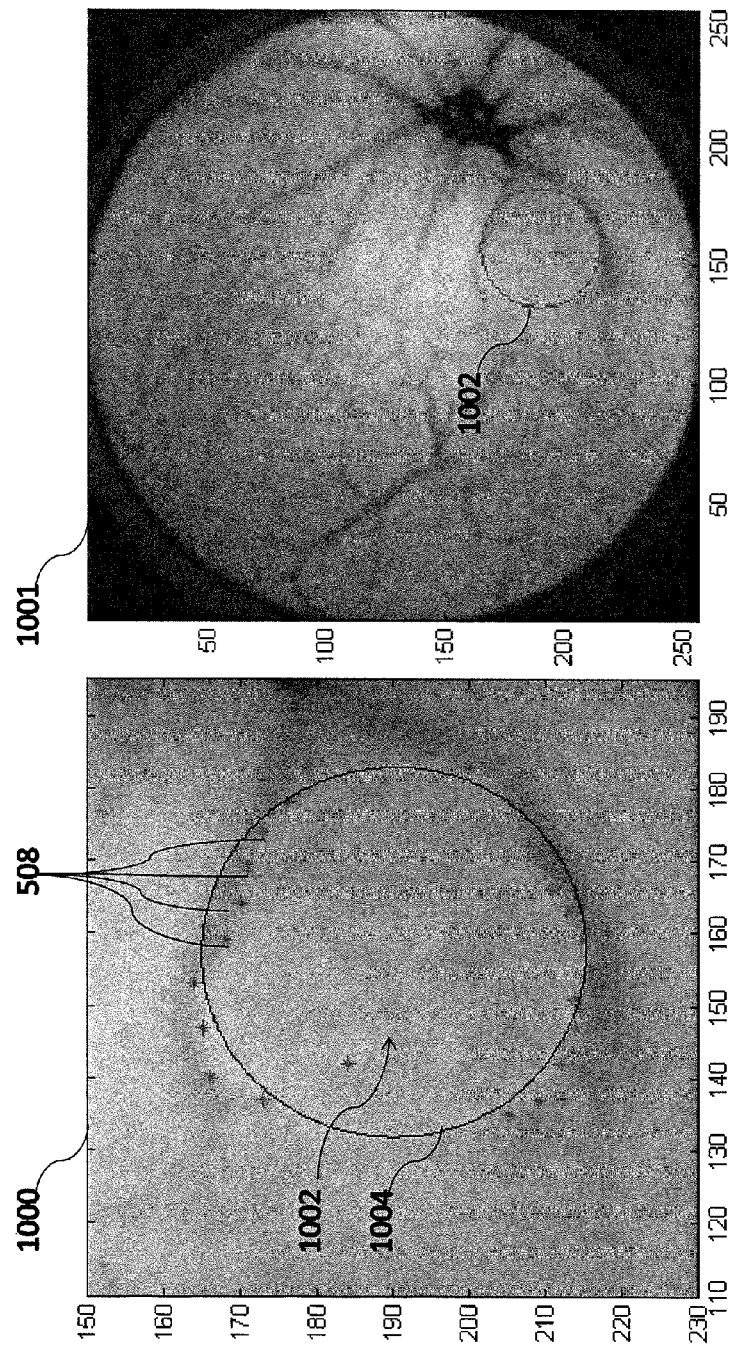
FIG. 10 shows a candidate polyp having an edge defined by an ellipse, according to an embodiment of the present invention.

Since outlier edge points may skew the estimation of the elliptical polyp shape, e.g., by a square of the error when using least squares approximation, the outlier points may be removed before estimating the polyp ellipse, e.g., as described in reference to FIG. 10.

Reference is made to FIG. 10, which shows a candidate polyp 1002 having an edge defined by an ellipse 1004, according to an embodiment of the present invention.

FIG. 10 shows a close-up view of the image region 1000 and a full view of the entire image frame 1001.

The processor may generate ellipse 1004 by computing a least squares approximation of an ellipse that fits polyp edge points 508. The processor may compute the least squares approximation by solving the following linear system of equations (2):

$$(2X_1 \ast X_2 X_2^2 X_1 X_2 - 1_n) \begin{pmatrix} P_{12} \\ P_{22} \\ q_1 \\ q_2 \\ r \end{pmatrix} = -X_1^2 \quad (2)$$

where $P_{12}$ and $P_{22}$ are the values of the (1,2) and (2,2) indices of the P matrix in equation (1), $q_1$ and $q_2$ are the $1^{st}$ and $2^{nd}$ indices of the Q matrix in equation (1), $X_1$ and $X_2$ are the x and y coordinate vectors each of dimension n×1 defining all n detected polyp edge points 508, and $1_n$ denotes a vector of n scalar values that equal 1. The operator ".*" may define the multiplication of $X_1$ and $X_2$ values separately at each ith index. The processor may solve the system of linear equations (2) to generate a solution for the parameters $P_{12}$, $P_{22}$, $q_1$, $q_2$ and r in equation (1) defining ellipse 1004.

The processor may compute the area of ellipse 1004, for example, as follows:

$$\frac{\pi \cdot \left(r + \frac{1}{4} Q^T \cdot P^{-1} \cdot Q\right)}{\sqrt{P_{22} - P_{12}^2}}$$

The processor may compute the eigenvalues $\lambda_1$ and $\lambda_2$ of the P matrix.

Figure 11:
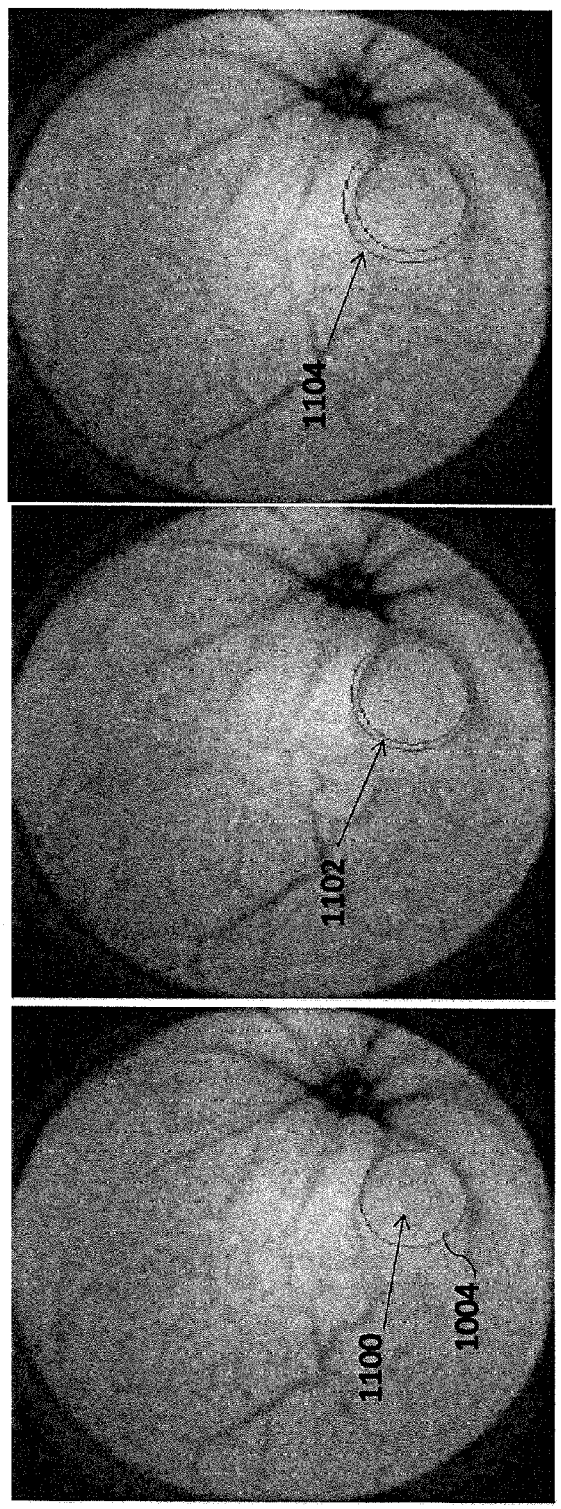
FIG. 11 shows an initial mask, a dilated mask and an expanded mask generated for each candidate polyp, according to an embodiment of the present invention.

Reference is made to FIG. 11, which shows an initial mask 1100, a dilated mask 1102 and an expanded mask 1104 generated for each candidate polyp 1002, according to an embodiment of the present invention.

Initial mask 1100 may be defined as the image region interior to ellipse 1004.

Dilated mask 1102 may be generated by dilating initial mask 1100 by a predetermined number of (N) pixels in each direction from the mask's center point. Dilated mask 1102 may be computed, for example, as mask4perim=imdilate (mask,strel('disk',N)) & ~mask & ROI_mask, using "imdilate" function provided in MATLAB's image processing toolbox.

Expanded mask 1104 may be generated by expanding dilated mask 1102 by a predetermined number of (M) pixels in each direction from the mask's center point. Expanded mask 1104 may be computed, for example, as mask4perim_expanded=imdilate(mask4perim,strel('disk', M)) & ~mask & ROI_mask.

In one example, masks 1100-1104 may be used to evaluate candidate polyps 1002 and calculate features, which distinguish between candidates that are probable polyps and candidates that are not.

The processor may eliminate or discard candidate polyps 1002 that satisfy one or more of the following conditions:

- If either of the eigenvalues $\lambda_1$ or $\lambda_2$ of the P matrix is negative, for example, indicating that candidate polyp 1002 is not shaped like an ellipse.
- If the eigenvalue ratio of the larger $\lambda_1$ to smaller $\lambda_2$ eigenvalues $\lambda_1/\lambda_2$ is larger than or equal to a predetermined threshold (e.g. 2.4), for example, indicating that candidate polyp 1002 is shaped like an elongated ellipse having a ratio of a main axis to a minor axis that is greater than or equal to a threshold ratio.
- If the area of ellipse 1004 is less than a predetermined threshold (e.g. 200 pixels, which is comparable to a circular candidate of radius of 8 pixels).
- The area of one or more of masks 1100-1104 is less than a minimum threshold number of pixels, e.g., mask4perim<10 pixels.

Other conditions may be used and any of the thresholds of the conditions may be set e.g. manually by a user operating input device (e.g. input device 24 of FIG. 1) or automatically by a processor (e.g. data processor 14 of FIG. 1) to minimize error calculations or based on system feedback.

In some cases, high polyp edge score may be erroneously detected near the edge of the image region of interest (ROI), for example, due to artifacts from the gradient change between the image and black ROI border. To remove such artifacts, the image ROI mask may be eroded or contracted radially inward by a predetermined number of pixels, e.g., 5 pixels. Polyp edge scores of image points outside of (radially outward from) the eroded ROI mask may be zeroed, for example, to eliminate such edge artifacts.

A dominant trait of polyps is their elliptical shape. Often, polyps are only partially elliptical. Typically, the more a candidate polyp 1002 confirms to the shape of an ellipse, the greater the certainty the candidate polyp 1002 is a polyp. To determine if a candidate polyp 1002 has an elliptical shape, the processor may detect the amount that the ellipse 1004 includes or intersects the candidate polyp 1002 edge. However, the above discussion generally relates to detecting the coincidence of polyp edge points 508 to a circle C (e.g. $PE = \nabla I^T \cdot (-\nabla C)$), thereby identifying candidate polyps 1002 having circular ellipse 1004 edges (e.g. as shown in FIGS. 10 and 11).

Figure 12:
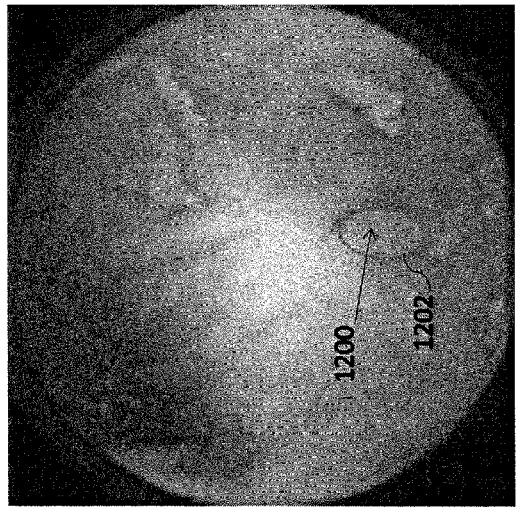
FIG. 12 shows a polyp having an elongated elliptical shape, according to an embodiment of the present invention.
Figure 12:
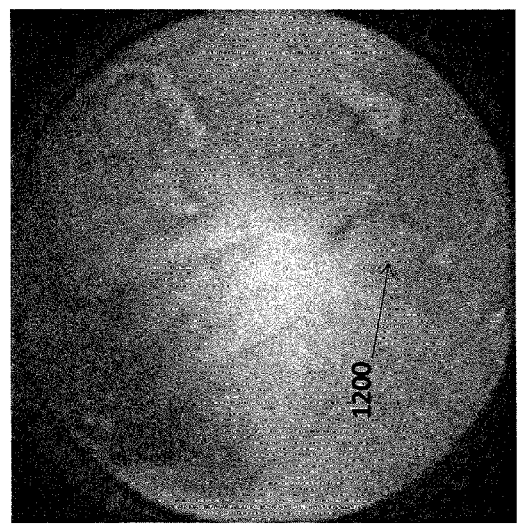

Reference is made to FIG. 12, which shows a polyp 1200 having an elongated elliptical shape 1202, according to an embodiment of the present invention. An elongated ellipse 1202 may have a main axis that is greater in length than its minor axis (e.g. a non-circular ellipse). Since polyps may also include elongated (non-circular) ellipses, it may be more accurate to identify candidate polyps 1200 using ellipse 1202 having a more general elongated elliptical edge E (which may or may not be circular). To identify candidate polyps 1200 having any elliptical shape, the processor may execute steps of the aforementioned method for an ellipse E instead of a circle C, for example, as follows.

The processor may compute polyp edge scores to be $PE = \nabla I^T \cdot (-\nabla E)$, which measures the coincidence of the gradient of the image brightness function I (e.g. the grayscale image) and the gradient of the elliptical function E. The benefit of comparing the gradient of the image function to the gradient of the ellipse E instead of circle C is in some examples significant, in particular, for polyps in the image function having a more elongated elliptical shape or for circular polyps in the image function having an actual polyp center point that is far from the initial guess of the center point of the circle C, for example, since the ellipse E has been fitted to the edges of the polyp candidate whereas the circle C has not.

For an elongated ellipse, detecting edge points along lines that are separated by a uniform grid of angles (e.g. lines 502 of FIG. 5 separated by angular intervals of $2\pi/N$ radians) may be inadequate, since the curvature of elongated ellipses is non-uniform. In some embodiments, uniformly sampling elongated ellipses may disproportionately increase sampling along relatively less curved or flatter, which in some cases may cause a false positive detection of parallel folds. To even the density of sampling, according to embodiments of the invention, highly curved regions of an elongated ellipse may be sampled at a greater rate (using more lines) to detect the relatively higher change in edge shape as compared to relatively low curvature regions of the elongated ellipse. In one embodiment, the processor may sample the polyp edges using a non-uniform array of lines, e.g., as described in reference to FIG. 13.

Figure 13:
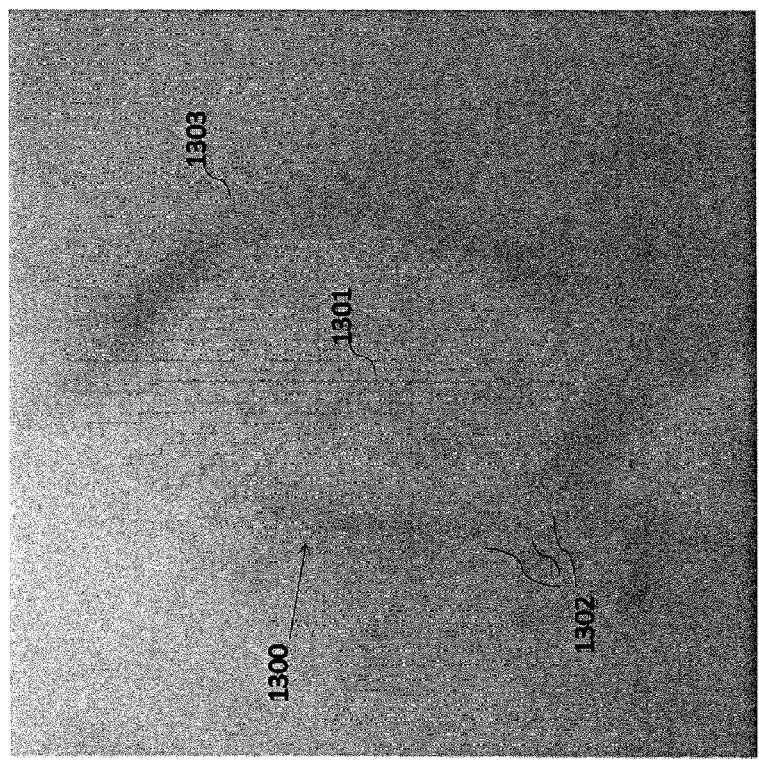
FIG. 13 shows an image of an elongated elliptical polyp and a plurality of non-uniform rays along which polyp edge scores may be analyzed, according to an embodiment of the present invention.

Reference is made to FIG. 13, which shows an image of an elongated elliptical polyp 1300 and a plurality of non-uniform rays 1302 along which polyp edge scores may be analyzed, according to an embodiment of the present invention. Rays 1302 are shown to zig-zag to confirm to the pixelation of the image, but may also be linear traversing the relevant pixels. There may be a higher density of rays 1302 near areas of elongated elliptical polyp 1300 that have a relatively greater curvature. FIG. 13 shows that rays 1302 along relatively higher curvature regions of polyp 1300 (e.g. the top and bottom regions of the imaged polyp) are more dense or more closely spaced than rays 1302 along relatively lower curvature regions of polyp 1300 (e.g. the left and right sides of the imaged polyp).

Rays 1302 may initially be generated in a unit circle u having a uniform grid of radial lines (e.g. lines 502 of FIG. 5). The initial unit circle u may define a grid including a plurality of (e.g. N=32) radial lines projecting from the center point $x_c$ of unit circle u at angular intervals of $2\pi/N$ radians. For example, unit circle u may be defined as $$u = \begin{bmatrix} \cos(t) \\ \sin(t) \end{bmatrix}, t = 0: \frac{2\pi}{N} : 2\pi - \frac{2\pi}{N}.$$

In this example, the unit circle u is constrained to have a radius of magnitude of less than or equal to one, although any other magnitude may be used.

The unit circle u may then be stretched or transformed into an ellipse to generate a non-uniform grid of rays 1302. For example, the ellipse may be generated as follows:

ellipse={$x_c + A \cdot u | \|u\|_2 \leq 1$}, where $x_c = -P^{-1} \cdot Q$ defines the center point $x_c$ of an initial unit circle u, $A = \text{sqrtm}((Q^T \cdot P^{-1} \cdot Q + 2r) \cdot P^{-1})$ defines a transformation A elongating or stretching the unit circle into the ellipse.

For each of the N angles, a ray 1302 may be generated having coordinates between a center point 1301 of the ellipse and an end point 1303 of the ray. The distance between center point 1301 and end point 1303 (the length) of each ray 1302 may be, e.g., approximately or on average greater than (e.g. 1.5 times) the radius of the ellipse along the ray at that angle. Thus, each ray 1302 may be longer than the radius to sample points both inside and outside the polyp 1300 edge.

Figure 14:
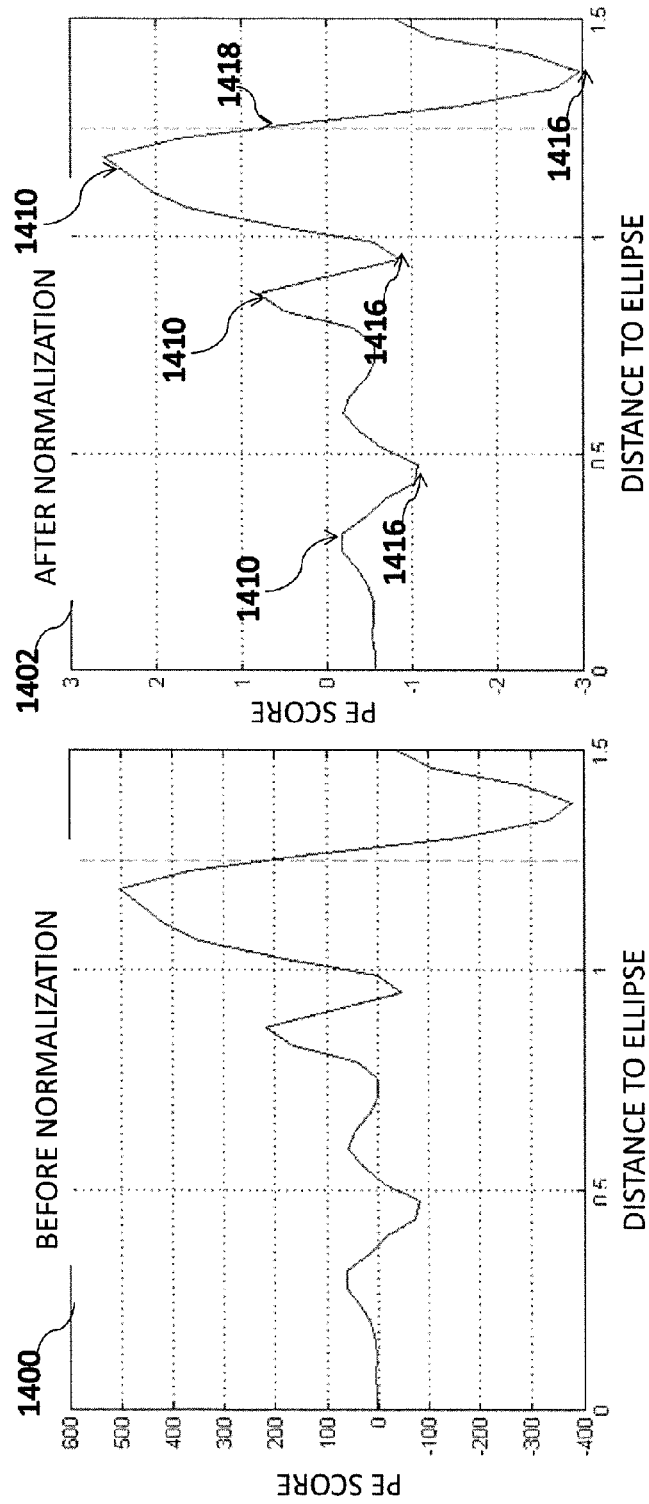
FIG. 14 includes graphs of raw and normalized polyp edge scores investigated along one of the rays of FIG. 13, according to an embodiment of the present invention.

Reference is made to FIG. 14, which includes graphs 1400 and 1402 of polyp edge scores investigated along one of the rays 1302 of FIG. 13, according to an embodiment of the present invention. Graph 1400 shows raw polyp edge scores and graph 1402 shows normalized polyp edge scores. The scores on the ray may be normalized to have a mean or average of 0 and a standard deviation of 1. The mean and standard deviation may be calculated for a segment or sub-portion of ray 1302, for example, from center point 1301 to a point radially inward from end point 1303 (e.g. having a distance of 1.25 times the radius of the ellipse along the ray at that angle). Polyp edge scores along the end segment of ray 1302 may be ignored since such segments do not typically belong to the candidate polyp 1300 and thus, may skew the normalization.

The processor may search each ray 1302 for candidate edge points that have polyp edge scores that are a local maximum and greater than or equal to the polyp edge scores of all radially inward points along ray 1302 (e.g. the greatest local maxima so far).

For all such candidate edge points, the processor may calculate one or more of the following features:

Min_between2maxima 1416, which is the minimal polyp edge score between the current candidate point and a previous candidate point (or a center point 1301 if the current candidate point is the most radially inward candidate point). Min_between2maxima 1416 detects the scores of a local minimum polyp edge score between local maxima 1410 polyp edge scores of two candidate edge points.

Diff_min_between2maxima_prev_max 1418, which is the difference between Min_between2maxima 1416 and the polyp edge score of the previous (radially inward) candidate point 1410 (or center point 1401 if the current candidate point is the most radially inward candidate point). Diff_min_between2maxima_prev_max 1418 may calculate the difference between a local maximum score 1410 and a subsequent local minimum score 1416 to determine the difference between scores of a candidate edge point and its radially outward neighboring minimum point. A high Diff_min_between2maxima_prev_max 1418 may indicate a significant peak followed by a significant trough in polyp edge scores moving radially outward along ray 1302, which indicates the associated candidate edge point may be located along a prominent edge.

Final_score, which estimates the likelihood a point is on the edge of the polyp, is calculated as a soft-margin of a Radial Basis Function (RBF) classifier whose features are Diff_min_between2maxima_prev_max and the ellipse distance. To determine the soft-margin Final_score, a training set may be assembled to include verified polyp edges and exclude rejected polyp edges based on these two features. A classifier (e.g. a support vector machine (SVM) classifier) may be trained on the training set to generate soft-margin function of the two features (e.g. a non-linear two-dimensional function), the values of which may be the soft-margin Final_score of the classifier. The function may be used as a decision rule to separate between the verified and false polyp edges—e.g., the higher the Final_score, the higher a probability is determined that the candidate is a polyp edge.

The processor may determine the edge point along each ray 1302 to be the point from among the candidate edge points along ray 1302 that has the highest Final_score (e.g. at 1.2 the distance to the ellipse in the example of FIG. 14). The processor may eliminate candidate edge points that are substantially close to center point 1301 (e.g. if dist2ellipse<0.65 or another predetermined threshold) and outlier edge points, for example, having a radius Rx that is greater than a predetermined threshold, e.g. 3/2 of a nominal radius $\overline{Rx}$ or smaller than a predetermined threshold, e.g. 2/3 of the nominal radius. The processor may detect up to N (e.g., N=32) edge points.

The edge points may be represented as a logical vector of N true/false or 0/1 values denoting if an edge point was/was not detected along each of the N rays 1302, and/or indicating the coordinates or distance of the detected edge point along each ray 1302.

Figure 15:
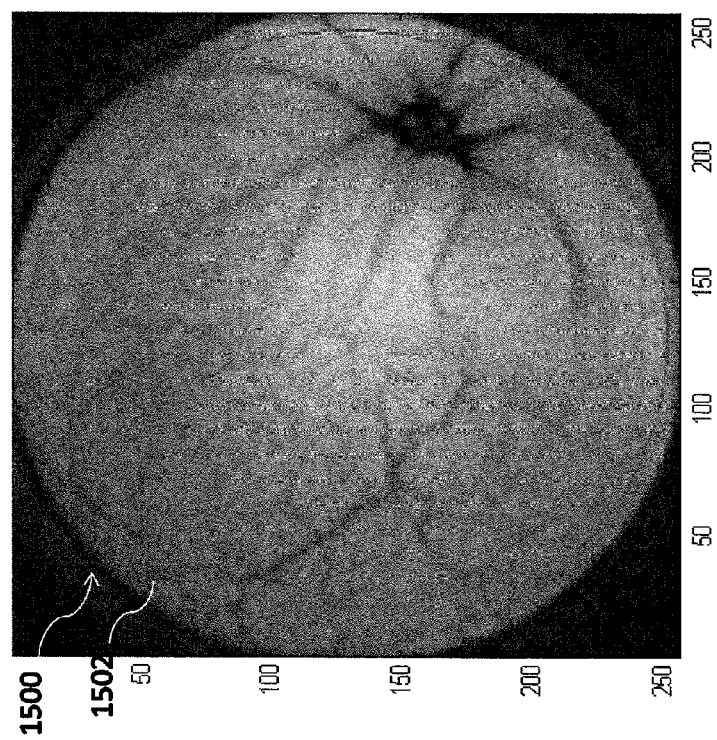
FIG. 15 shows a region outside of the image region of interest (ROI) and an eroded mask within the image ROI, according to an embodiment of the present invention.

Reference is made to FIG. 15, which shows a region 1502 outside of the image region of interest (ROI) and an eroded mask 1502 within the image ROI, according to an embodiment of the present invention. In some cases, high polyp edge score may be erroneously detected near the edge of region 1502 and the image ROI, for example, due to artifacts from the gradient change between the image and black ROI border. To remove such artifacts, the processor may generate eroded mask 1502 by eroding or contracting the image ROI radially inward by a predetermined number of pixels, e.g., 8 pixels. The processor may filter or eliminate candidate edge points radially outward from eroded mask 1502, for example, by changing the associated value in the logical vector from true to false, or by zeroing the associated polyp edge scores.

Additionally or alternatively, the processor may filter or discard any candidate edge points along a ray 1302 surrounded on both sides by adjacent rays 1302 having no candidate edge points. In one embodiment using a logical vector representation for edge points, a true logical value associated with an angle may be changed to a false logical value if the true value is in between two false values associated with adjacent rays 1302 or angles.

Additionally or alternatively, the processor may filter or discard any candidate edge point along a ray 1302 which is an outlier compared to neighboring candidate edge points. For every candidate edge point along a ray 1302 (e.g. associated with a true logical value), the processor may calculate a ratio of the distance between center point 1301 and the candidate edge point and the distance between center point 1301 and a neighboring candidate edge point. The neighboring candidate edge point is the neighboring point having the minimal value of the two neighbors. The ratio may be defined as the larger distance divided by the smaller distance, e.g., such that the ratio is ≥1. For rays 1302 that have only one neighboring candidate edge point (e.g. that form a pair) and that have a ratio that is greater than a predetermined threshold value (e.g. 1.21), the one of the two candidate edge points that is farther from center point 1301 may be discarded. For rays 1302 that have two neighbors and that have a ratio that is greater than a predetermined threshold value (e.g. 1.17), the center candidate edge point is discarded.

Additionally or alternatively, the processor may filter or discard consecutive candidate edge points that approximate a straight line, since straight lines may usually be associated with in vivo tissue folds rather than polyp edges. For example, the processor may identify all contiguous sequences of candidate edge points having no gaps of missing edge points. The processor may test each sequence to detect if the sequence of candidate points approximates a line and, if so, discards the sequence. If the sequence includes at least a predetermined number of (N) (e.g. seven) candidate edge points (associated with at least N respective angles/rays 1302), the processor may calculate a least squares approximation measuring the fit of the (N) points X to a line (e.g. y=a*x+b) for example, by solving the following system of linear equations for line parameters a and b.

$$[-X \quad -1_n] \cdot \begin{bmatrix} a \\ b \end{bmatrix} = -y \tag{3}$$

The error of the least squares approximation may be inversely proportional to how closely the sequence approximates a line. For example, a sequence with a below threshold error may be discarded. The error of the least squares approximation may be defined, for example, as:

$$E = \frac{\left[[-X \quad -1_n] \cdot \begin{bmatrix} a \\ b \end{bmatrix} + y\right]^2}{R_p}, \; R_p = \sqrt{\frac{\# \text{ pixels in mask}}{\pi}}, \quad (4)$$

where $R_p$ is the estimated radius of the polyp. The number of pixels in mask is a measure of the area A of the polyp mask and is related to the radius of the polyp $R_p$ by the equation $A=\pi R_p^2$. The processor may define the following error parameters:

"Max error no end": Max{E(2:N−1)}, which defines the maximum error of all candidate edge points in the sequence except the end points of the sequence, 1 and N.

"Max distance end": Max{ellipse_dist_(1 N)}, which defines the maximum error of the end points of the sequence, 1 and N. The processor may filter or discard an entire sequence of candidate edge points that satisfy for example one or more of the following conditions:

"Max error no end"≤0.5
  "Max distance end"≥1.13
  "Max distance end"≥5/9*"Max error no end"+49/45

Other or different conditions or filtering operations may be used. In some example tests, an average of 220 candidate polyps were detected per image frame. In order to confirm likely or probable candidate polyps and reject erroneous candidate polyps, features or traits of each candidate polyp may be analyzed.

The processor may define an "angle" feature, which may be calculated based on the amount of the detected candidate polyp edge that coincides with the approximated ellipse, for example by sampling the candidate polyp edge using a non-uniform array of rays 1302 (e.g. as shown in FIG. 13). The angle feature calculation may be determined, for example, as a largest contiguous angle in which the detected candidate polyp edge coincides with the approximated ellipse, or the angle in which a non-contiguous area is not counted.

The processor may define a "fold" feature to identify folds or blood vessels (such as, arteries or blood vessels) inside the edge of a polyp candidate, which may cause false identification of the polyp candidate as a pathology. Fold or blood vessel features and their associated fold score may be defined. Folds scores/values may be assigned to image area elements to represent the fitting of the image area elements to predetermined criteria that characterize folds, such that, for example, high fold score assigned to an image area element correspond to high probability that the image area element shows a fold or a fold segment. Folds in the imaged tissue may be characterized by lower color brightness values and higher color saturation levels in greater depths of the fold, for example since smaller amount of white light enters the fold. Additionally, the folds areas have characteristic distribution of color saturation with higher color saturation levels in greater depths of the fold. The characteristic distribution of color saturation can be pre-identified and a fold template of color saturation distribution may be determined accordingly. For example, a folds score or rating can be assigned to an image area element based on the identified color brightness values below the predetermined threshold, color saturation levels and correlation between the color saturation distribution and the predetermined fold template. For example, the fold score may be calculated by multiplying the identified color brightness values below the predetermined threshold by the corresponding saturation levels in the same image area elements and by the correlation between the color saturation distribution and the predetermined fold template in the same image area elements. The correlation between the color saturation distribution and the predetermined fold template may be calculated by a correlation function as known in the art.

Folds or blood vessels may resemble polyp edges and are thus a common root cause of false alarms for detecting polyp edges. Since the magnitude of the fold or blood vessel score of the edges of a candidate polyp may be highly variable, the fold score may be defined based on a relative measure of the polyp edge. In one embodiment, the processor may sample points from the polyp edge in order to quantify the magnitude of the polyp edge. In some embodiment, points detected to be on the polyp edge based on the angle feature may be verified or replaced based on the fold feature, e.g., as described in reference to FIG. 16.

Figure 16:
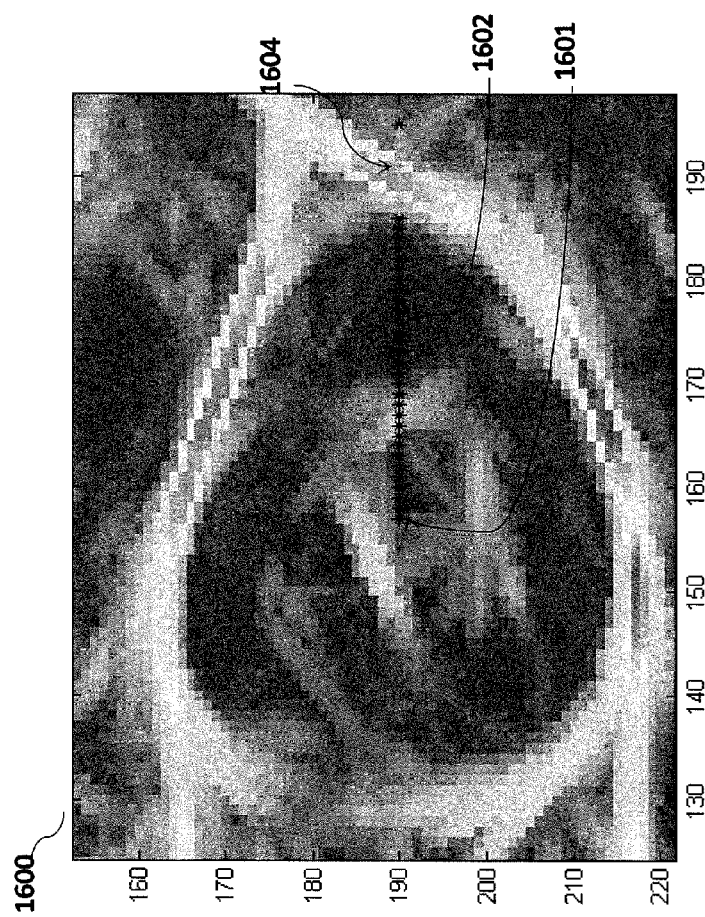
FIG. 16 shows an image of fold scores of a candidate polyp image region, according to an embodiment of the present invention.

Reference is made to FIG. 16, which shows an image of fold scores 1600 of a candidate polyp image region, according to an embodiment of the present invention. In order to measure the gradient magnitude of the polyp edge, the location of the polyp edge may be fine-tuned along each ray 1602. The processor may search a segment 1604 of points along each ray 1602 neighboring the initial candidate edge point to verify or replace each candidate edge point. Ray segment 1604 may extend from the initial candidate edge point radially outward a predetermined number of (e.g. 7) pixels along the associated ray 1602 (or to the end point of the ray, whichever is closer) and/or may extend radially inward a predetermined number of pixels (e.g. 3 pixels). The new candidate edge point may be a point with a maximal fold score along ray segment 1604. Fold score image 1600 may be refined, as described in reference to FIG. 17.

Figure 17:
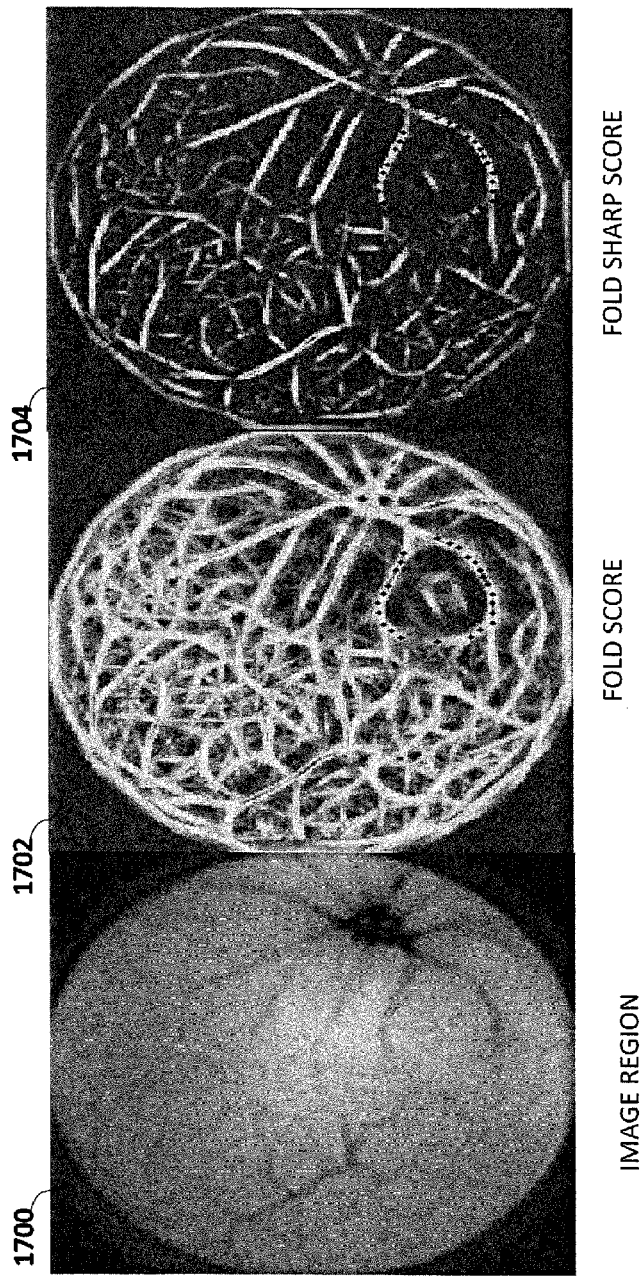
FIG. 17 shows an in-vivo image, an associated fold score image, and an associated fold sharp score image, according to an embodiment of the present invention.

Reference is made to FIG. 17, which shows an in-vivo image 1700, an associated fold score image 1702, and an associated fold sharp score image 1704, according to an embodiment of the present invention. The processor may refine fold score image 1702 to generate fold sharp score image 1704, using for example the following morphological operation: Folds_sharp(Folds−imopen(Folds,strel('disk', N))).*ROI_mask. The Folds_sharp operation may reduce fold scores so that scores for thin folds and blood vessels are below threshold and disappear, after which the scores may be increased to accentuate the remaining folds and blood vessels in fold sharp score image 1704. The threshold for a fold/blood vessel score may be the minimum of a predetermined constant value (e.g. 0.2) and a predetermined percentile (e.g. the 43$^{rd}$ percentile) of the Folds_sharp scores. The processor may apply the threshold to generate a binary image (e.g. the right image in FIG. 18) that depicts the coincidence of folds/blood vessels and the candidate edge points. Since fold feature detects the integrity of candidate edge points, not the polyp edge itself, the actual fold sharp score image 1704 may be expanded, e.g., by a logical condition that ellipse_dist≥0.25 or another predetermined threshold, wherein ellipse_dist is defined as sqrt((X'*P*X+0.25*q'*inv(P)*q)/(r+0.25*q'*inv(P)*q)). This distance is determined to be equal 1 at the center of the ellipse, 0 on the perimeter and negative outside the ellipse. To filter artifacts at the edge of the image ROI, the fold sharp score image 1704 may be multiplied by a contracted ROI mask 1802, e.g., as described in reference to FIG. 18.

Figure 18:
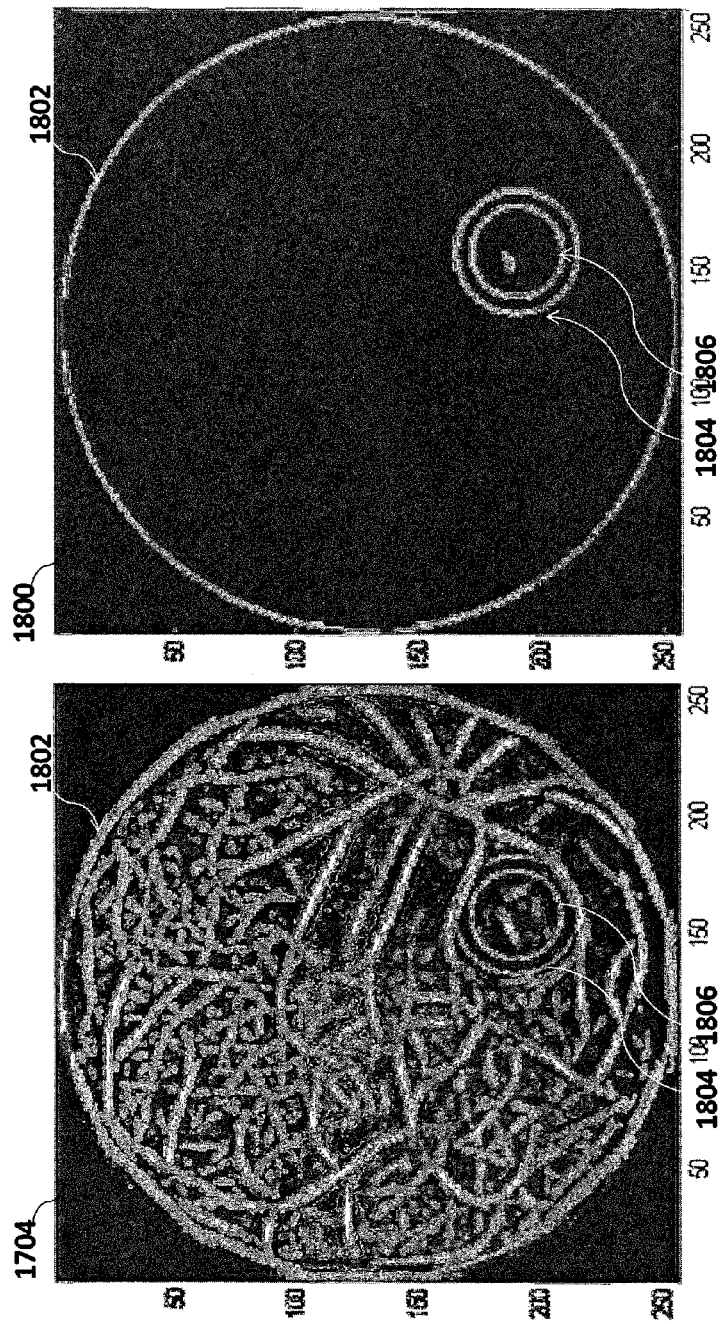
FIG. 18 shows the fold sharp score image of FIG. 17 overlaid with a contracted ROI mask, an ellipse mask, and a contracted ellipse mask, according to an embodiment of the present invention.

Reference is made to FIG. 18, which shows the fold sharp score image 1704 of FIG. 17 overlaid with a contracted ROI mask 1802, an ellipse mask 1804, and a contracted ellipse mask 1806, according to an embodiment of the present invention. The contracted ROI mask 1802 may generated by contracting or reducing the ROI mask radially inward by a first predetermined number of (e.g. 5) pixels and the contracted ellipse mask 1806 may be generated by contracting or reducing the ellipse mask 1804 radially inward by a second predetermined number of (e.g. 5) pixels.

The final fold score "Folds_sharp" may define if there is a fold or blood vessel through the center of the polyp and, in some embodiments, the degree of certainty or the prominence of the fold or blood vessel.

Figure 19:
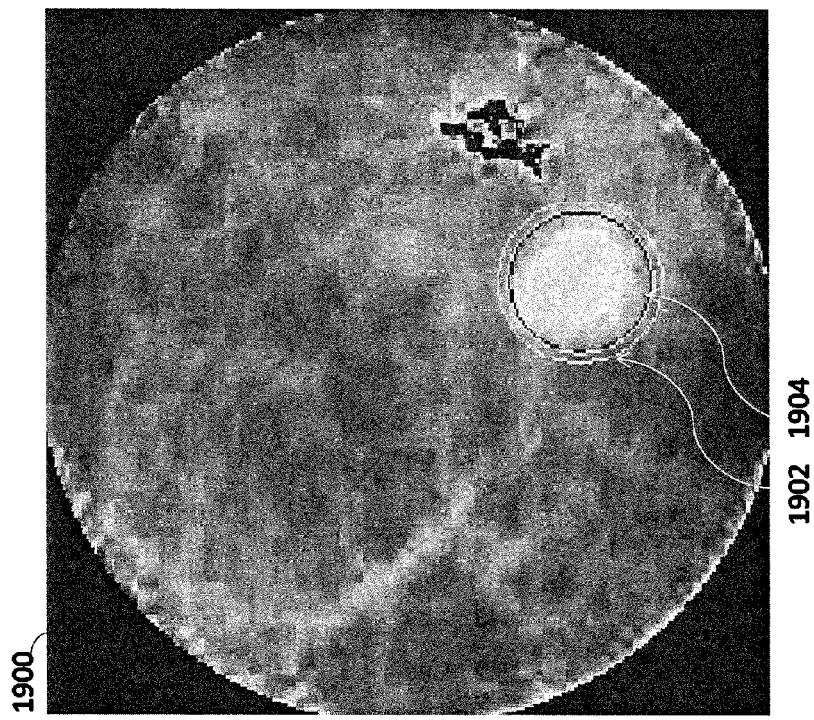
FIG. 19 shows a hue score image, according to an embodiment of the present invention.

The processor may define a "hue" feature, e.g., as described in reference to FIG. 19.

Reference is made to FIG. 19, which shows a hue score image 1900, according to an embodiment of the present invention. The hue feature score may be computed, for example, as follows:

$$\frac{avg[H(\text{mask})]}{avg[H(\text{mask4perim})] + 0.01}$$

where avg[H(mask)] measures the average hue inside the ellipse mask 1904 (e.g. inside the candidate polyp) and avg[H(mask4perim)] measures the average hue of a dilated mask 1902 (e.g. including the candidate polyp and the polyp edge). Hue is typically lower inside a polyp (avg[H(mask)]) than along its edge (avg[H(mask4perim)]). For example, a candidate polyp may be verified when the hue score is less than a predetermined constant, e.g. 1 (and rejected when the hue score is greater than a predetermined constant, e.g. 1). In one example, a small constant (e.g. 0.01) is added to the denominator so that the denominator is greater than zero and the hue score is always defined.

Figure 20:
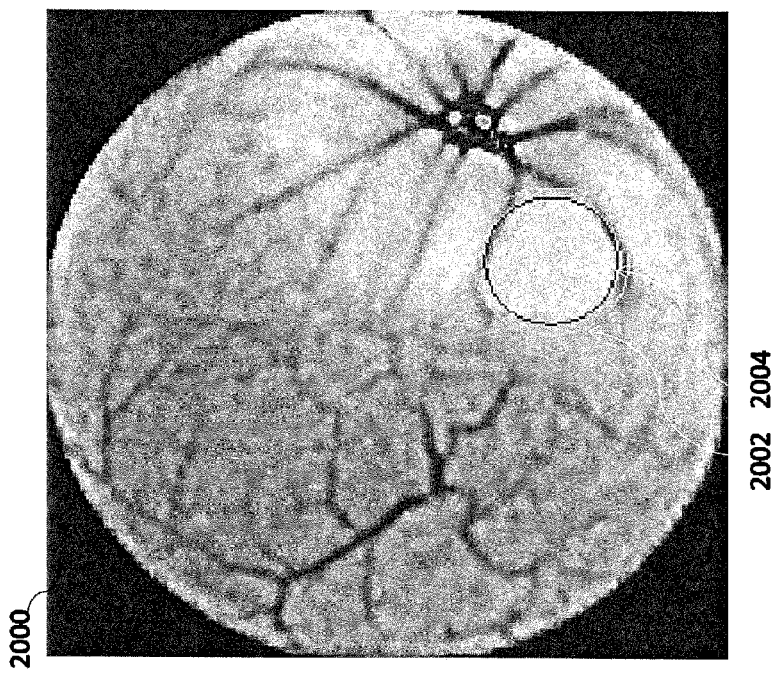
FIG. 20 shows a saturation score image, according to an embodiment of the present invention.

The processor may define a "saturation" feature, e.g., as described in reference to FIG. 20.

Reference is made to FIG. 20, which shows a saturation score image 2000, according to an embodiment of the present invention. The saturation feature score may be computed, for example, as follows:

$$\frac{avg[S(\text{mask})]}{avg[S(\text{mask4perim})] + 0.01}$$

where avg[S(mask)] measures the average saturation inside the ellipse mask 2004 (e.g. of candidate polyp) and avg[S(mask4perim)] measures the average saturation of a dilated mask 2002 (e.g. including the candidate polyp and the polyp edge). Saturation is typically lower inside a polyp (e.g. in avg[S(mask)]) than along its edge (e.g. in avg[S(mask4perim)]). For example, a candidate polyp score may be increased when the saturation score is less than or equal to 1 (and rejected when the saturation score is greater than 1). Other or different methods of computing this and other scores may be used.

Figure 21:
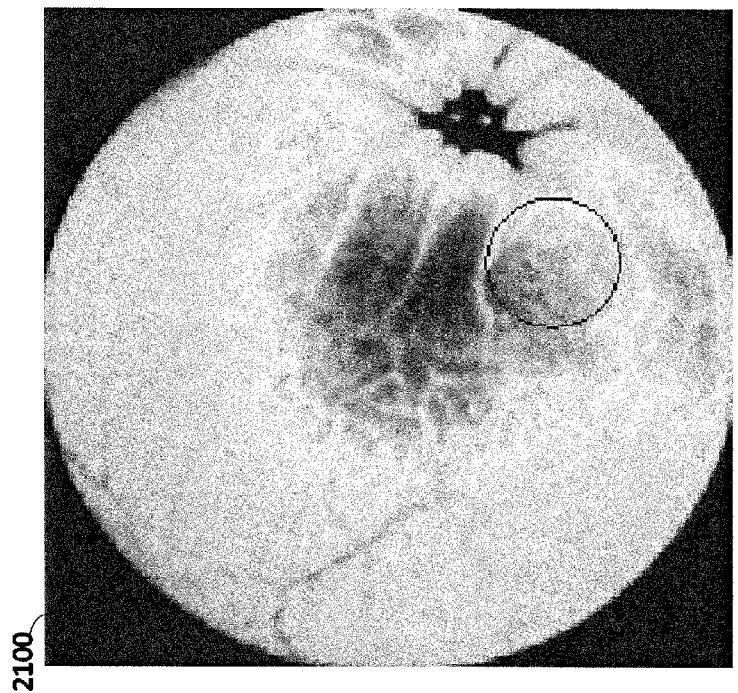
FIG. 21 shows an intensity score image, according to an embodiment of the present invention.

The processor may define an "intensity" feature, e.g., as described in reference to FIG. 21.

Reference is made to FIG. 21, which shows an intensity score image 2100, according to an embodiment of the present invention. The intensity of a polyp is typically relative high compared to other structures, for example, since polyps generally protrude from the luminal wall and are thus closer to the illumination source and the imager. The intensity feature score may be computed, for example, as follows:

$$avg[I(\text{mask})]$$

where avg[I(mask)] measures the average intensity inside the ellipse mask 2102 (e.g. inside the candidate polyp). Since the intensity of a polyp is typically relatively high, a candidate polyp may be verified when its intensity score is relatively high or above a threshold (and rejected when the intensity score is relatively low or below a threshold).

Figure 22:
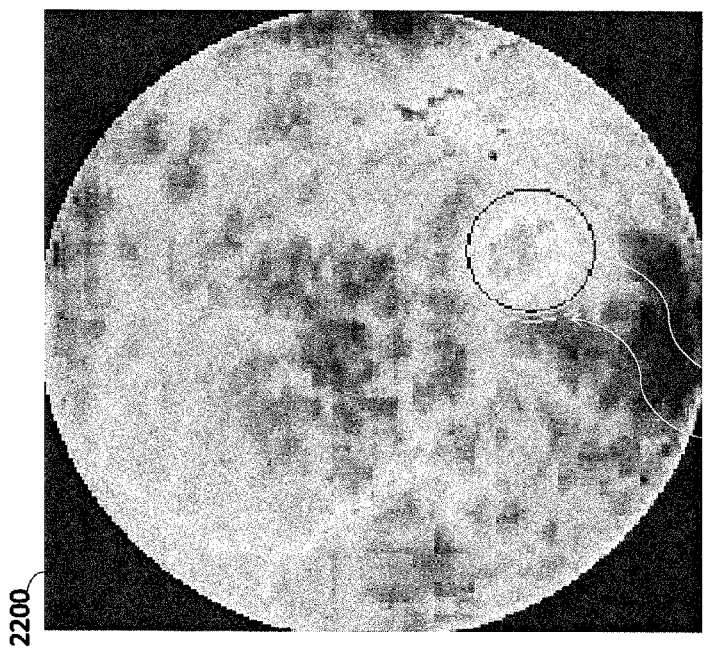
FIG. 22 shows a red score image, according to an embodiment of the present invention.

The processor may define a "red" feature, e.g., as described in reference to FIG. 22.

Reference is made to FIG. 22, which shows a red score image 2200, according to an embodiment of the present invention. The red feature score may be computed, for example, as follows:

$$\frac{avg[\text{Red}(\text{mask})]}{avg[\text{Red}(\text{mask4perim})] + 0.01}$$

where avg[Red(mask)] measures the average red inside the ellipse mask 2204 (e.g. of candidate polyp) and avg[Red(mask4perim)] measures the average red of a dilated mask 2202 (e.g. including the candidate polyp and the polyp edge). A polyp is typically redder inside its edge (e.g. in avg[Red(mask)]) than along its edge (e.g. in avg[Red(mask4perim)]). For example, a candidate polyp may be verified when the red score is greater than 1. For false candidate polyps in which a blood vessel resembles a polyp edge, the blood vessel edge may be significantly redder than a typical polyp edge, causing the red score to be atypically low. For example, a candidate polyp may be rejected when the red score is less than 1. In some embodiment, the red score may be defined, for example, as by identifying features indicative of the probability of pathology in candidate regions, and calculating a score for an image based on the identified features. Identification of red regions is performed according to a red criterion value in image regions, which may be determined according to location of color of an image region in a color space relative to pre-calculated border in the color space. The pre-calculated border may distinguish between a red portion and a non-red portion of the color space, and the distance of the color from the pre-calculated border may correspond to a red criterion value. The red score corresponds to the candidate score of the candidate region with the highest probability of pathology in the image.

Figure 23:
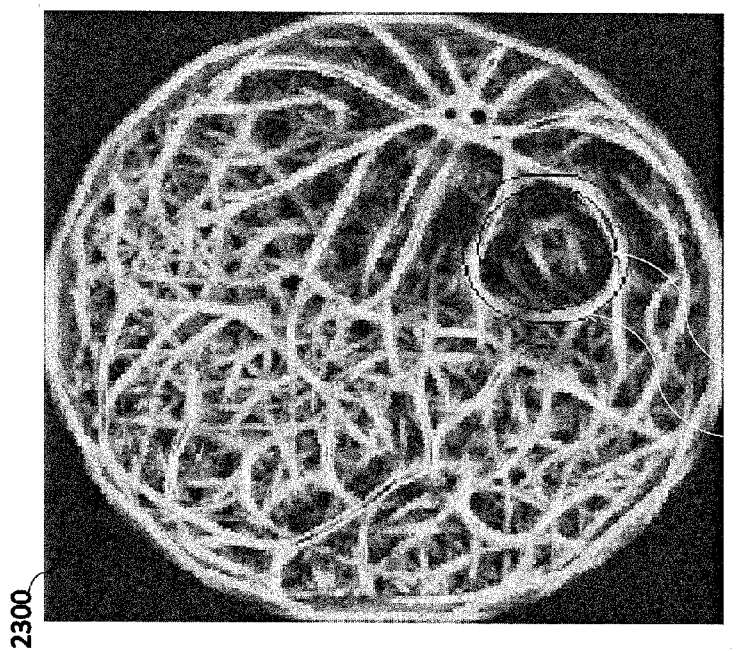
FIG. 23 shows an edge perimeter score image, according to an embodiment of the present invention.

The processor may define an "edge perimeter" feature, e.g., as described in reference to FIG. 23.

Reference is made to FIG. 23, which shows an edge perimeter score image 2300, according to an embodiment of the present invention. The edge perimeter score may be computed, for example, as the $10^{th}$ percentile of folds score in a dilated mask 2302 (e.g. mask perim-expanded) e.g. where 100th percentile corresponds to a maximum fold score. The edge perimeter score may bolster polyps with weak edges (e.g. having low fold scores), but where the edges are elliptical (e.g. having fold scores in the dilated mask 2302 defining the elliptical edge). The edge perimeter score may promote polyps that are close to full ellipses.

Figure 24:
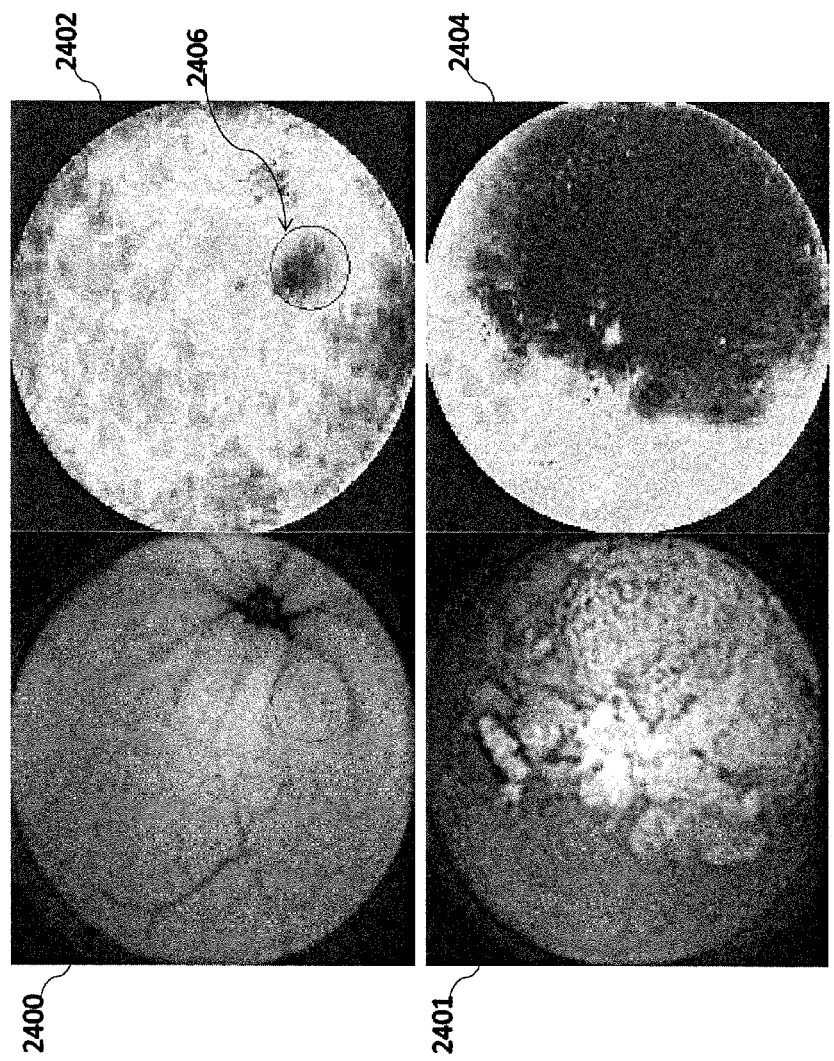
FIG. 24 shows images and associated content score images, according to an embodiment of the present invention.

The processor may define a "content" feature, e.g., as described in reference to FIG. 24.

Reference is made to FIG. 24, which shows images 2400 and 2401 and associated content score images 2402 and 2404, respectively, according to an embodiment of the present invention. Content may be defined herein as any foreign substance e.g. food particles, bubbles, etc., non-native to the luminal passageway. Most polyps typically do not have content on them. However, there may be a small population of polyps that do have content stuck to them or surrounding them, and for which this content is their dominant trait. Polyp candidates with content may be rejected or have lowered scores. The processor may generate one or more of the following content scores:

A minimum content score in mask 2406. Since the content inside a polyp is typically relatively low, a candidate polyp may be verified when its content score is relatively low or below a threshold (and rejected when the content score is relatively high or above a threshold).

The 10th percentile of the content score in mask 2406 is used to validate or increase the image score for images with candidate polyps having less than 10% content.

Figure 25:
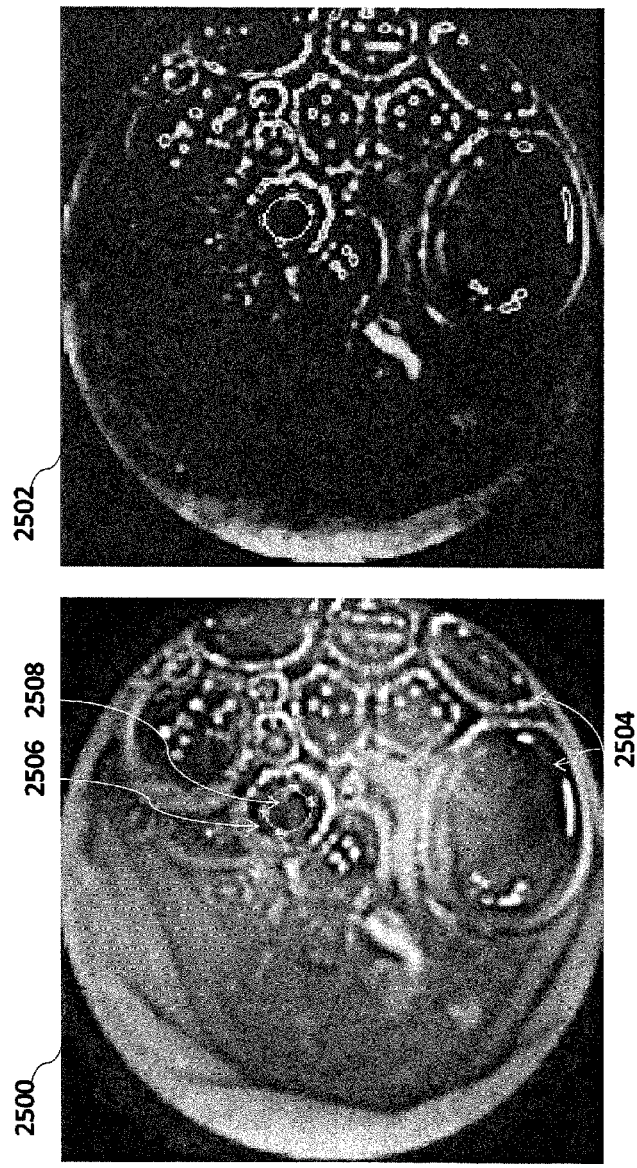
FIG. 25 shows an image and an associated white score image, according to an embodiment of the present invention.

The processor may define a "white" feature, e.g., as described in reference to FIG. 25. The white feature may be used to eliminate false candidate polyps that are bubbles.

Reference is made to FIG. 25, which shows an image 2500 and an associated white score image 2502, according to an embodiment of the present invention. Image 2500 includes bubbles 2502. Since bubbles 2502 are generally elliptical, bubbles 2502 may cause false alarms as candidate polyps. However, unlike polyps, bubbles 2502 typically reflect light from the imager producing white glare within the elliptical ring. Accordingly, to detect if a candidate polyp should be rejected as a bubble 2502, the processor may detect if the candidate has any or a significant amount of white inside its edge. The processor may generate an eroded mask 2508, for example, using MATLAB's imerode function which erodes the image, and MATLAB's strel function which creates morphological structuring element, as mask4interior=imerode (mask,strel('disk',M)) & ROI_mask defining the polyp interior (excluding the perimeter edge), for example, eroded by a predetermined number of (M) pixels in each direction from elliptical mask 2506. The processor may define the white feature as the maximum white score inside the polyp, e.g., in mask4interior, to detect if there is white inside the candidate polyp. Since white inside the elliptical edge typically indicates the candidate is a bubble 2502 and not a polyp, a candidate polyp may be rejected when its white score is non-zero or above a threshold (and verified when the white score is zero or below a threshold). A high white score may indicate a high probability that a candidate region is covered by a bubble and thus, for example, the probability that the candidate region is a red pathology region decreases. The white score may be calculated, for example, based on light intensity values and differences between the R, G and B brightness values, wherein a combination of high light intensity value and small differences between the R, G and B brightness values in an image area element correspond to high white score value of the image area element. However, in case the light intensity value in the image area element is low and/or the difference between at least one couple among the R, G and B brightness values in the image area element is high, a low white score value will be assigned to the analyzed image region. In one exemplary embodiment, the formula for determining the white score may have the following form (other suitable formulas may be used):

$$[(R+G+B)/3]-\text{Max}\{|R-G|,|R-B|,|B-G|\}$$

wherein R, G and B are the R, G and B brightness values in an image represented using R, G and B color components values.

Figure 26:
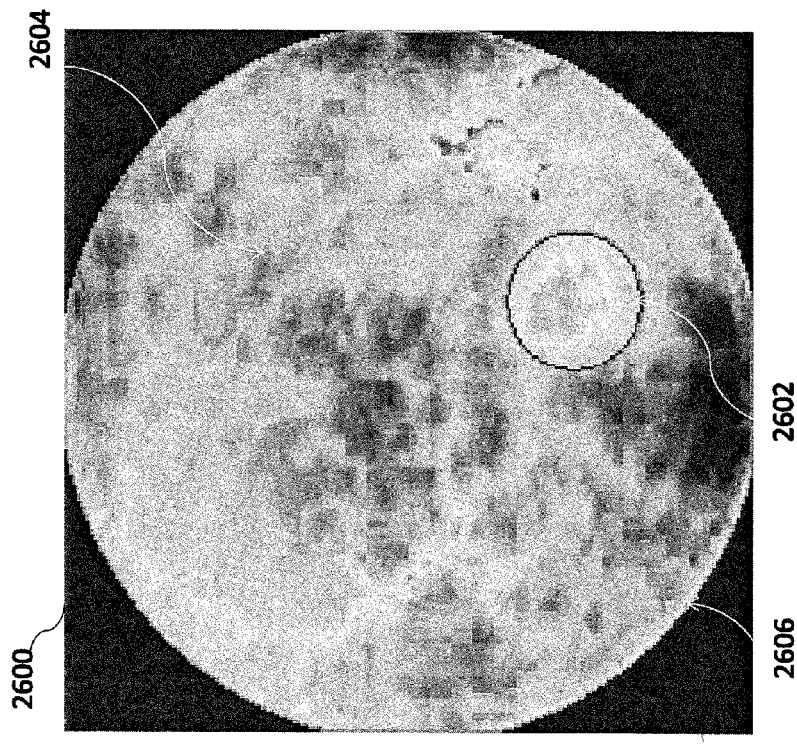
FIG. 26 shows a relative red score image, according to an embodiment of the present invention.

The processor may define a "relative red" feature comparing the red score inside and outside a candidate polyp/mask, e.g., as described in reference to FIG. 26.

Reference is made to FIG. 26, which shows a relative red score image 2600, according to an embodiment of the present invention. The processor may define an ellipse mask 2602 (e.g. defining the region of the candidate polyp) and the region exterior to the mask 2604 (e.g. defining the region exterior to the candidate polyp). The region exterior to the mask 2604 may be defined as the difference between the ROI mask 2606 and ellipse mask 2602, e.g., not_mask=~mask & ROI_mask. The relative red feature score may be computed, for example, as follows:

$$\frac{avg[\text{Red(mask)}]}{avg[\text{Red(not mask)}] + 0.01}$$

where avg[Red(mask)] measures the average red inside ellipse mask 2602 (e.g. inside the candidate polyp) and avg [Red(not mask)] measures the average red outside of mask 2602 (e.g. outside the candidate polyp). Since a polyp is typically redder (e.g. in avg[Red(mask)]) than healthy tissue in the image (e.g. in avg[Red(not mask)]), a candidate polyp may be verified when the relative red score is greater than a predetermined threshold, e.g. 1 (and rejected when the relative red score is less than a predetermined threshold, e.g. 1). As with other formulas disclosed herein, other or different methods may be used to compute the red feature score.

The processor may use a classifier to compile and combine the scores of one or more of the features, e.g., polyp edge feature, angle feature, fold feature, hue feature, saturation feature, intensity feature, red feature, edge perimeter feature, content feature, white feature, and/or relative red feature. The processor may normalize features to have a mean of 0 and a standard deviation of 1, for example, based on a training set of images. The processor may input feature scores for one or more candidate polyps in an image frame into the classifier. The processor may combine all the feature scores for all candidate polyps into an overall image score that is for example the maximum score of all candidates. The processor may divide images into groups of images that are verified to include polyps (1) (e.g. having an above threshold overall image score) or rejected as not including polyps (−1) (e.g. having a below threshold overall image score). Images with verified polyps may be displayed together with rejected images or separately therefrom and may be ordered e.g. chronologically or according to its overall image scores, e.g., from highest to lowest scores. The threshold may be determined by using a set of images predetermined to include polyps or not, and training the classifier to match the results of the training set. In some embodiments, the classifier may indicate a probability or degree of severity of a polyp in the image frame based on the image score, for example, indicating a percentage likelihood that a frame has a polyp and/or the size or shape of the polyp such as small vs. large or round edge vs. wrinkled edge. The processor may identify and/or mark/flag each image frame that has at least one verified candidate polyp.

Figure 27:
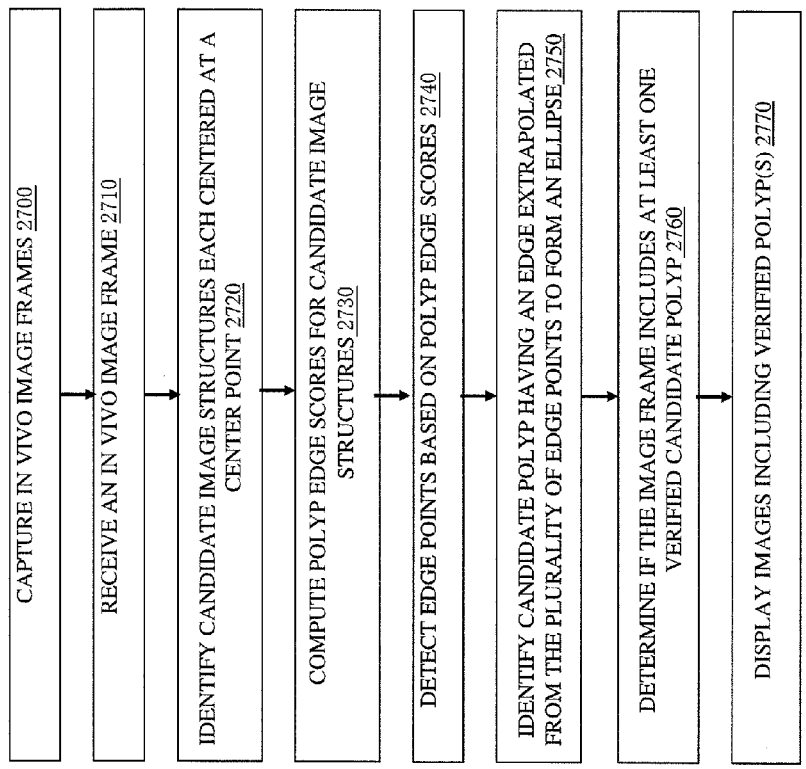
FIG. 27 is a flowchart of a method for identifying one or more candidate polyps in an in-vivo image frame, according to an embodiment of the invention.

Reference is made to FIG. 27, which is a flowchart of a method for identifying one or more candidate polyps in an in-vivo image frame, according to an embodiment of the invention. Note that while the operations are described as being performed in sequence, they may be performed partially in parallel, or in a pipeline fashion.

In operation 2700, an autonomous imaging device (e.g., imaging device 40 of FIG. 1) may capture in vivo images while passively traversing a body lumen, such as, the GI tract. The imaging device may include a transmitter, which may wirelessly transmit captured images while traversing the body lumen from inside a patient's body to a receiver disposed outside the patient's body. The captured images may be stored in a memory or storage unit (e.g., image database 10 or storage unit 19 of FIG. 1) from which the processor may access the captured images.

In operation 2710, a processor (e.g., data processor 14 of FIG. 1) may receive the in vivo images from the memory or storage unit.

In operation 2720, the processor may identify one or more candidate imaged structures each centered at a center point of a respective circle or ellipse. In one example, the center points may be positioned in predetermined image coordinates, or in predetermined positions in the image, and arranged as a grid (e.g. as shown in FIG. 3).

In operation 2730, the processor may compute polyp edge scores for a plurality of points of each candidate imaged structure, each polyp edge score measuring the coincidence of the respective candidate imaged structure and its respective circle or ellipse at that point. In one example, the polyp edge score is computed to be a function of the product of the gradient of the image $\nabla I$ and the gradient of the ellipse $\nabla E$ centered at the center point, such as, $PE = \nabla I^T \cdot (-\nabla E)$.

In operation 2740, for each candidate imaged structure, the processor may use the polyp edge scores to detect a plurality of edge points imaged structure in each of a plurality of respective radial directions from the center point of the ellipse (e.g. along respective rays 1302 of FIG. 13). For each radial direction, the processor may identify each point that has a local maximum polyp edge score (e.g. polyp edge score 510 of FIG. 7) that is greater than all previous local maximum polyp edge scores for radially inward points, and that has a neighboring point located radially outward from the point along the radial direction that has a local minimum polyp edge score (e.g. right-most polyp edge score 516 at pixel radius 32 of FIG. 7) as a potential or candidate edge point. The detected edge point in each radial direction may be the candidate edge point that has the greatest difference between the greatest local maximum polyp edge score so far and a local minimum of a following neighboring point (e.g. difference 518 of FIG. 7).

In operation 2750, the processor may identify a candidate polyp for each candidate imaged structure for which extrapolating the detected edge points forms an edge in a shape approximating an ellipse.

In operation 2760, the processor may identify image frames that include at least one verified candidate polyp, e.g., where the image has an above threshold overall image score. The processor may generate a plurality of feature scores for a plurality of respective features for each of one or more candidate polyps in each image. The processor may combine the plurality of feature scores for all of the one or more candidate polyps in the image to generate an overall image score. Using a classifier, the processor may identify images that have at least one verified candidate polyp based on the overall image score.

In operation 2770, the processor may mark the identified image frames including verified polyps. A monitor (e.g., monitor 18 of FIG. 1) may display each marked image including at least one verified polyp. The monitor may display the verified polyp images in (1) a standard playback mode e.g. playing the entire image sequence including polyp and non-polyp images, where the verified polyp images are highlighted or marked and/or (2) an abridged polyp image playback mode e.g. playing only the subset of verified polyp images and skipping the non-polyp images. The monitor may display polyp feature scores, the image score, additional polyp information, such as, estimated polyp size, location, color and shape, and/or related information, such as, a computer-determined diagnosis or related information which may be suggested to a user.

Operations 2700-2770 may be repeated for each image, i, in a set of image frames (i=1, . . . , N) of the captured image stream.

Other operations, orders of operations, and methods of identifying one or more candidate polyps in one or more in-vivo image frames may be used. Various specific sets of methods may be combined in different embodiments and the operations of FIG. 27 may be executed alone or in combination with other processes described herein.

Manually entering visual annotation of polyps from an image stream captured by an imaging device may be laborious due to the typically large number of image frames (e.g., 50,000 frames) collected as it passes through the GI tract. Furthermore, visual analysis by a physician may depend on the particular viewing physician and may be non-standardized, for example, providing differences based on human variation, when compared to other patient records or a previous image stream taken of the same patient.

Accordingly, embodiments of the invention may generate an automated and standardized system to optimally analyze and annotate polyps in images of the GI tract.

Some embodiments of the invention may be utilized to selectively provide automatic or semi-automatic detection of in-vivo images (or image frames of an in-vivo image stream), corresponding to polyps. Some embodiments of the invention may allow a physician or operator to selectively view and/or rapidly access in-vivo images that correspond to polyps (e.g., for diagnosis purposes, to locate or determine the presence of a polyp for further investigation as benign or malignant, or the like). Computer-generated analysis is generally used to provide information to a physician and not replace the ultimate diagnosis by a physician, who may run additional tests or have an opinion that conflicts with the computer-generated analysis. Some embodiments of the invention may allow shortening of viewing time required by a physician for diagnosis, and/or shortening of time required by a physician to access and/or selectively view in-vivo images that include to polyps. Some embodiments of the invention may allow a selective display (or other presentation) of a portion (e.g., a relatively small portion, or multiple small portions) of an in-vivo image stream, which corresponds to polyp scenes (a sequential image sequence of the same individual polyp or group of polyps). Some embodiments of the invention may allow a physician to determine a portion-of-interest of an in-vivo image stream which the physician may examine, e.g., to detect a portion of an in-vivo image stream which corresponds to polyps and/or polyp scenes, for example, for further inspection by the physician. Some embodiments of the invention may allow to "skip" (e.g., by fast-forwarding) one or more portions of an in-vivo image stream based on polyp information, e.g., portion(s) that correspond to polyps and/or polyp scenes of interest, portion(s) that do not correspond to polyps and/or polyp scenes of interest, portions that correspond to existence of polyps and/or polyp scenes, portions that correspond to absence of polyps and/or polyp scenes, portions that correspond to large, raised, irregularly shaped and/or red polyps, portions that correspond to polyps in a specified location such as colon polyps, etc. Some embodiments of the invention may allow a physician to concentrate or "focus" his examination of an in-vivo image stream on a portion-of-interest, e.g., based on polyp information that corresponds to the portion-of-interest.

When used herein, a "score" may be a general rating of a quality or evaluation.

When used herein, a scene, sequence, or anatomical event may for example, include a plurality of frames depicting an in-vivo event such as one or more polyps or any other sequence. Each scene or sequence may have the same or different length(s).

Although embodiments of the invention describe assigning image scores to each frame, scores may similarly be assigned to each candidate polyp, region of a frame, frame quadrant, individual pixel or pixel set, for example, of a 4×4 or 16×16 pixel block.

The frames may be analyzed for scoring in a non-compressed form (analyzing absolute pixel values) and/or a compressed form (analyzing changes and relative pixel values). A compressed data header or other summary frame information package may indicate associated score value(s). Compression mechanisms known in the art for expressing spatial changes within a frame or temporal changes between consecutive frames may be used.

It may be appreciated that although the frame analysis may be made after processing, frames may also be analyzed in "real-time" during frame capture and transmission.

It may be appreciated that an image or frame may be a digital or analog representation of real-life objects and that reference to objects in the frame may refer to the visual representation of those objects. For example, a lumen or characteristic of the lumen (such as the presence, location, size, color and shape of polyps) in an image may refer to a region of pixels in the image that visually represent a real-life lumen.

It is noted that while embodiments of the invention described herein are adapted for imaging of the GI tract, the devices and methods disclosed herein may be adapted for imaging other body cavities or spaces.

The foregoing description of the embodiments of the invention has been presented for the purposes of illustration and description. It is not intended to be exhaustive or to limit the invention to the precise form disclosed. It should be appreciated by persons skilled in the art that many modifications, variations, substitutions, changes, and equivalents are possible in light of the above teaching. It is, therefore, to be understood that the appended claims are intended to cover all such modifications and changes as fall within the true spirit of the invention.

What is claimed is:

1. A method of identifying one or more candidate polyps in an in-vivo image frame, the method comprising:
    receiving an image frame of a body lumen captured in vivo;
    determining one or more center points of candidate imaged structures, each center point defining a respective circle;
    computing polyp edge scores for a plurality of points around each center point, each polyp edge score measuring the coincidence of a respective candidate imaged structure and its respective circle;
    for each center point:
        detecting a plurality of edge points of the respective candidate imaged structure based on the polyp edge score;
        identifying a candidate imaged structure based on the detected edge points, and
    for each candidate imaged structure, identifying a candidate polyp for which extrapolating the detected edge points forms an edge in a shape approximating an ellipse.

2. The method of claim 1 comprising:
    generating one or more feature scores for one or more respective features for each of one or more candidate polyps in the image frame;
    combining the feature scores for each of the candidate polyps in the image to generate an overall image score; and
    identifying that the image frame includes at least one verified candidate polyp if the overall image score satisfies a predetermined threshold.

3. The method of claim 2, wherein at least one of the feature scores is computed to be a function of the amount of the detected candidate polyp edge that coincides with the approximated ellipse.

4. The method of claim 2 comprising indicating a probability that the image frame includes a polyp in the image based on the overall image score.

5. The method of claim 4 comprising measuring the amount of the detected candidate polyp edge that coincides with the approximated ellipse by sampling the candidate polyp edge using a non-uniform array of lines.

6. The method of claim 1, wherein the polyp edge score is computed to be a function of the product of the gradient of the image and the gradient of the circle centered at the center point.

7. The method of claim 1 comprising:
    for each candidate imaged structure:
        computing a polyp edge score for points of the candidate imaged structure located along a ray extending radially outward from the center point; and
        detecting at most one edge point along each of a plurality of rays, wherein the detected edge point is the point along each ray that has the greatest difference between the greatest local maximum polyp edge score so far and a local minimum of a following neighboring point.

8. The method of claim 1, wherein the ray has a predetermined length approximating an upper bound of a radius of a typical large polyp.

9. The method of claim 1 comprising removing outlier edge points having radii that substantially differs from the radii of the majority of the other edge points.

10. A system for identifying one or more candidate polyps in an in-vivo image frame, the system comprising:
    a memory to store an image frame of a body lumen captured in vivo by an in vivo imaging device; and
    a processor to determine one or more center points of candidate imaged structures, each center point defining a respective circle, and compute polyp edge scores for a plurality of points around each center point, each polyp edge score measuring the coincidence of a respective candidate imaged structure and its respective circle, wherein for each center point the processor is to detect a plurality of edge points of the respective candidate imaged structure based on the polyp edge score and identify a candidate imaged structure based on the detected edge points, and wherein for each candidate imaged structure the processor is to identify a candidate polyp for which extrapolating the detected edge points forms an edge in a shape approximating an ellipse.

11. The system of claim 10, wherein the processor is to generate one or more feature scores for one or more respective features for each of one or more candidate polyps in the image frame, combine the feature scores for each of the candidate polyps in the image to generate an overall image score, and identify that the image frame includes at least one verified candidate polyp if the overall image score satisfies a predetermined threshold.

12. The system of claim 11, wherein the processor is to compute at least one of the feature scores to be a function of the amount of the detected candidate polyp edge that coincides with the approximated ellipse.

13. The system of claim 11, wherein the processor is to determine a probability that the image frame includes a polyp in the image based on the overall image score.

14. The system of claim 13, wherein the processor is to measure the amount of the detected candidate polyp edge that coincides with the approximated ellipse by sampling the candidate polyp edge using a non-uniform array of lines.

15. The system of claim 10, wherein the processor is to compute the polyp edge score to be a function of the product of the gradient of the image and the gradient of the circle centered at the center point.

16. The system of claim 10, wherein for each candidate imaged structure the processor is to compute a polyp edge score for points of the candidate imaged structure located along a ray extending radially outward from the center point, and detect at most one edge point along each of a plurality of rays, wherein the detected edge point is the point along each ray that has the greatest difference between the greatest local maximum polyp edge score so far and a local minimum of a following neighboring point.

17. The system of claim 10, wherein the ray has a predetermined length approximating an upper bound of a radius of a typical large polyp.

18. The system of claim 10, wherein the processor is to remove outlier edge points having radii that substantially differs from the radii of the majority of the other edge points.

19. The system of claim 11 further comprising a display to display the image frame identified to include at least one verified candidate polyp.

20. The system of claim 19, wherein the display further displays location, size, shape or color information associated with one or more candidate polyps in the displayed image frame.

* * * * *